(12) United States Patent
Park et al.

(10) Patent No.: US 9,035,825 B2
(45) Date of Patent: May 19, 2015

(54) PORTABLE BIOMETRIC MONITORING DEVICES HAVING LOCATION SENSORS

(71) Applicant: Fitbit, Inc., San Francisco, CA (US)

(72) Inventors: James Park, Berkeley, CA (US); Heiko Gernot Albert Panther, Oakland, CA (US); Shelten Gee Jao Yuen, Berkeley, CA (US)

(73) Assignee: Fitbit, Inc., San Francisco, CA (US)

(*) Notice: Subject to any disclaimer, the term of this patent is extended or adjusted under 35 U.S.C. 154(b) by 0 days.

(21) Appl. No.: 14/265,202

(22) Filed: Apr. 29, 2014

(65) Prior Publication Data

US 2014/0292565 A1 Oct. 2, 2014

Related U.S. Application Data

(63) Continuation of application No. 14/242,711, filed on Apr. 1, 2014.

(60) Provisional application No. 61/807,279, filed on Apr. 1, 2013.

(51) Int. Cl.
*G01S 19/00* (2010.01)
*H04N 5/232* (2006.01)
*H04N 7/18* (2006.01)
*H04L 29/08* (2006.01)

(52) U.S. Cl.
CPC .............. *G01S 19/00* (2013.01); *H04L 67/125* (2013.01); *H04N 5/23206* (2013.01); *H04N 7/185* (2013.01)

(58) Field of Classification Search
USPC ................ 342/357.2, 357.25, 357.29, 357.28
See application file for complete search history.

(56) References Cited

U.S. PATENT DOCUMENTS

| | | | |
|---|---|---|---|
| 5,828,336 A | 10/1998 | Yunck et al. | |
| 6,583,369 B2 | 6/2003 | Montagnino et al. | |
| 7,558,678 B2 | 7/2009 | Jones | |
| 7,570,962 B2* | 8/2009 | Chou | 455/456.5 |
| 7,616,153 B2 | 11/2009 | Honda et al. | |
| 7,706,977 B2* | 4/2010 | Soehren | 701/541 |
| 8,417,300 B2* | 4/2013 | Wong et al. | 455/575.1 |

(Continued)

FOREIGN PATENT DOCUMENTS

EP 1 721 237 8/2012

OTHER PUBLICATIONS

U.S. Appl. No. 14/242,711, filed Apr. 1, 2014, Park et al.

(Continued)

*Primary Examiner* — Harry Liu
(74) *Attorney, Agent, or Firm* — Weaver Austin Villeneuve & Sampson LLP

(57) ABSTRACT

Assisted-GPS for a portable biometric monitoring device is provided. The portable biometric monitoring device may obtain updated ephemeris data from an associated secondary device via a short-range, low-power communication protocol. The secondary device may be a computing device such as a smartphone, tablet, or laptop. Various rules may control when the ephemeris data is updated. The ephemeris data may be used in the calculation of the global position of the portable biometric monitoring device. Additionally, the portable biometric monitoring device may communicate downloaded position fixing data to the associated secondary device. The associated secondary device may then calculate the global position from the position fixing data.

13 Claims, 13 Drawing Sheets

(56) References Cited

U.S. PATENT DOCUMENTS

| | | | |
|---|---|---|---|
| 8,630,798 B2* | 1/2014 | Hani et al. | 701/408 |
| 8,762,059 B1* | 6/2014 | Balogh | 701/533 |
| 2002/0168985 A1 | 11/2002 | Zhao et al. | |
| 2009/0303118 A1 | 12/2009 | Corazza et al. | |
| 2009/0315773 A1 | 12/2009 | Tomita | |
| 2010/0062792 A1 | 3/2010 | Han et al. | |
| 2010/0187406 A1 | 7/2010 | Van Dalen et al. | |
| 2010/0273419 A1* | 10/2010 | Rajagopal et al. | 455/41.2 |
| 2010/0331145 A1 | 12/2010 | Lakovic et al. | |
| 2011/0032105 A1 | 2/2011 | Hoffman et al. | |
| 2011/0163914 A1* | 7/2011 | Seymour | 342/357.42 |
| 2011/0267230 A1 | 11/2011 | LaMance et al. | |
| 2011/0282168 A1* | 11/2011 | Weiss et al. | 600/323 |
| 2012/0253663 A1* | 10/2012 | Hani et al. | 701/431 |
| 2012/0274508 A1 | 11/2012 | Brown et al. | |
| 2012/0303390 A1* | 11/2012 | Brook et al. | 705/4 |
| 2013/0106684 A1 | 5/2013 | Weast et al. | |
| 2013/0138458 A1* | 5/2013 | Lorsch | 705/3 |
| 2013/0159223 A1 | 6/2013 | Bahl et al. | |
| 2013/0215229 A1* | 8/2013 | Yerli | 348/46 |
| 2014/0160033 A1* | 6/2014 | Brikman et al. | 345/173 |
| 2014/0179298 A1 | 6/2014 | Grokop et al. | |
| 2014/0180621 A1 | 6/2014 | Poduri et al. | |
| 2014/0275850 A1 | 9/2014 | Venkatraman et al. | |
| 2014/0292564 A1 | 10/2014 | Park et al. | |
| 2014/0292566 A1 | 10/2014 | Park et al. | |
| 2014/0293059 A1 | 10/2014 | Park et al. | |
| 2014/0316305 A1 | 10/2014 | Venkatraman et al. | |

OTHER PUBLICATIONS

U.S. Appl. No. 14/265,205, filed Apr. 29, 2014, Park et al.
U.S. Appl. No. 14/265,208, filed Apr. 29, 2014, Park et al.
"Activator is One of the Best Cydia iPhone Hacks | Control your iPhone with Gestures," IPhone-tips-and-advice.com, [retrieved on Jul. 9, 2013 at http://www.iphone-tips-and-advice.com/activatior.html], 10 pp.
"Assisted GPS," (updated Mar. 31, 2014) in: Wikipedia, the free encyclopedia, [Retrieved on Apr. 2, 2014, downloaded at http://en.wikipedia.org/wiki/Assisted GPS], 4 pages.
Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.
DesMarais, Christina (posted on Sep. 3, 2013) "Which New Activity Tracker is Best for You?" Health and Home, Health & Fitness, Guides & Reviews, [Retrieved on Sep. 23, 2013 at http://www.techlicious.com/guide/which-new-activity-tracker-is-right-for-you/] 4 pp.
Empson, Rip, (Sep. 22, 2011) "Basis Reveals An Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch Sync," (Mar. 2009), Garmin Ltd., 56 pp.
Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
"Global Positioning System," (updated Mar. 29, 2014) in: Wikipedia, the free encyclopedia, [Retrieved on Apr. 2, 2014, downloaded at http://en.wikipedia.org/wiki/Global Positioning System], 23 pages.
"GPS navigation device," (updated Mar. 26, 2014) in: Wikipedia, the free encyclopedia, [Retrieved on Apr. 2, 2014, downloaded at http://en.wikipedia.org/wiki/GPS navigation device], 8 pages.
"GPS signals," (updated Apr. 1, 2014) in: Wikipedia, the free encyclopedia, [Retrieved on Apr. 2, 2014, downloaded at http://en.wikipedia.org/wiki/GPS signals], 12 pages.
Larklife, User Manual, (2012) Lark Technologies, 7 pp.
Lark/Larkpro, User Manual, (2012) "What's in the box," Lark Technologies, 7 pp.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
US Office Action, dated Jul. 9, 2014, issued in U.S. Appl. No. 14/242,711.
US Office Action, dated Jul. 17, 2014, issued in U.S. Appl. No. 14/265,205.
US Office Action, dated Aug. 15, 2014, issued in U.S. Appl. No. 14/265,208.
US Office Action, dated Oct. 22, 2014, issued in U.S. Appl. No. 14/290,909.
US Advisory Action, dated Feb. 18, 2015, issued in U.S. Appl. No. 14/265,205.
US Notice of Allowance [Corrected Notice of Allowability], dated Mar. 20, 2015, issued in U.S. Appl. No. 14/265,208.
US Office Action, dated Apr. 7, 2015, issued in U.S. Appl. No. 14/561,092.
US Notice of Allowance, dated Jan. 29, 2015, issued in U.S. Appl. No. 14/290,909.
US Office Action, dated Feb. 25, 2015, issued in U.S. Appl. No. 14/290,912.

* cited by examiner

PORTABLE BIOMETRIC MONITORING DEVICES HAVING LOCATION SENSORS

CROSS-REFERENCE TO RELATED APPLICATIONS

This application is a continuation application of U.S. patent application Ser. No. 14/242,711, filed Apr. 1, 2014, titled "PORTABLE BIOMETRIC MONITORING DEVICES HAVING LOCATION SENSORS," which claims the benefit under 35 U.S.C. §119(e)(1) of U.S. Provisional Application No. 61/807,279, filed Apr. 1, 2013, titled "PORTABLE BIOMETRIC MONITORING DEVICE HAVING LOCATION SENSORS," both of which are hereby incorporated by reference in their entirety.

BACKGROUND

Recent consumer interest in personal health has led to a variety of personal health monitoring devices being offered on the market. Such devices, until recently, tended to be complicated to use and typically had few features and responded slowly.

Recent advances in sensor, electronics, and power source miniaturization have allowed the size of personal health monitoring devices, also referred to herein as "biometric tracking" or "biometric monitoring" devices, to be offered in small sizes that were previously impractical. For example, the Fitbit Ultra is a biometric monitoring device that is approximately 2" long, 0.75" wide, and 0.5" deep; it has a pixelated display, battery, sensors, wireless communications capability, power source, and interface button, as well as an integrated clip for attaching the device to a pocket or other portion of clothing, packaged within this small volume.

In some versions of personal health monitoring devices, GPS capabilities have been provided. Because GPS is a technology that was originally developed in the 1970s and 1980s to allow nuclear ballistic missile submarines to precisely know their locations in order to accurately target submarine-launched nuclear warheads, GPS does not always lend itself well to integration into modern consumer electronic devices. For example, by modern standards, the GPS system uses a very slow data transfer speed of 50 bits per second, which means that a GPS receiver, in some cases, has to be on for as long as 12 minutes before a GPS positional fix may be obtained. Once a positional fix is obtained, subsequent positional fixes may take much less time to obtain (assuming that the subsequent positional fix occurs within a sufficiently close interval), but this initial lock-on period requires that the GPS receiver be powered for the entire initial lock-on, which can be taxing on devices with small battery capacities.

SUMMARY

In some implementations, a method of determining a global position of a worn biometric monitoring device may be provided. The method may include: (a) determining that the worn biometric monitoring device does not have stored updated ephemeris data and (b) obtaining updated ephemeris data via a wireless short-range, low-power communication protocol from a secondary device associated with the worn biometric monitoring device.

In some such implementations of the method, the method may further include: (c) determining that a global position of the worn biometric monitoring device should be calculated and (d) calculating the global position of the worn biometric monitoring device using the ephemeris data obtained in (b).

In some such implementations, the worn biometric monitoring device may include a navigation data receiver and the calculation of the global position in (d) may include: (i) determining orbital positions of navigation satellites according to the ephemeris data obtained in (b), (ii) obtaining position fixing data via the navigation data receiver from the navigation satellites, and (iii) calculating the global position of the worn biometric monitoring device using the position fixing data obtained in (ii). In some such implementations, the method may further include: (iv) obtaining, before (i), from the associated secondary device, a last calculated global position of the associated secondary device. In some other or additional implementations of the method, (b) may include obtaining updated ephemeris data associated with the navigation satellites that transmitted position fixing data to the navigation data receiver.

In some other or additional implementations of the method, the secondary device may be a portable device.

In some other or additional implementations of the method, the short-range, low-power communication protocol may be selected from the group consisting of: Bluetooth, ANT, near field communication (NFC), ZigBee, IEEE 802.11, IEEE 802.15, Infrared Data Association (IrDA) protocols, and standards related to any of the foregoing.

In some other or additional implementations of the method, (a) may include: (i) determining a time remaining before stored ephemeris data is no longer current, (ii) comparing the time remaining determined in (i) to an ephemeris data update time threshold, and (iii) requesting updated ephemeris data from the secondary device when the time remaining is less than the ephemeris data update time threshold. In some such implementations, the ephemeris data update time threshold is a time less than 2 hours. In some other or additional implementations, (a) may further include, between (ii) and (iii), (iv) detecting that the secondary device is within communication range.

In some other or additional implementations of the method, the secondary device may obtain updated ephemeris data from a navigation satellite.

In some other or additional implementations of the method, the secondary device may obtain updated ephemeris data from an Earth-based organization serving updated ephemeris data.

In some other or additional implementations of the method, (b) may include obtaining X amount of days of ephemeris data and X is a number between 0 and 30.

In some other or additional implementations of the method, (a) may include determining that a more recently updated version of the ephemeris data stored on the worn biometric monitoring device is available and (b) may include obtaining the more recently updated version of the ephemeris data via the short-range, low-power communication from the secondary device associated with the worn biometric monitoring device.

In some implementations, a wearable biometric monitoring device may be provided. The wearable biometric monitoring device may include communication circuitry, the communication circuitry configured to receive ephemeris data from a secondary device associated with the wearable biometric monitoring device via a wireless short-range, low-power communication protocol and output the ephemeris data to a controller, and the controller including one or more processors and a memory, wherein the one or more processors, the memory, and the communication circuitry, are communicatively connected and the memory is configured to store ephemeris data and program instructions for controlling the one or more processors to: (a) determine that the stored ephemeris data in the memory is not updated, (b) obtain updated ephemeris data from the secondary device via the communication circuitry, and (c) calculate the global position of the wearable biometric monitoring device using the updated ephemeris data obtained in (b).

In some such implementations, the wearable biometric monitoring device may further include a navigation data receiver and wherein the calculating of the global position in (c) includes: (i) determining orbital positions of navigation satellites according to the updated ephemeris data obtained in (b), (ii) obtaining position fixing data via the navigation data receiver from the navigation satellites, and (iii) calculating the global position of the wearable biometric monitoring device using the position fixing data obtained in (ii). In some other or additional implementations, the wearable biometric monitoring device may further include: (iv) obtaining, before (i), from the associated secondary device, a last calculated global position of the associated secondary device. In some other or additional implementations, (b) includes obtaining updated ephemeris data associated with the navigation satellites that transmitted position fixing data to the navigation data receiver.

In some other or additional implementations, the secondary device is a portable device.

In some other or additional implementations, the short-range, low-power communication protocol is selected from the group consisting of Bluetooth, ANT, near field communication (NFC), ZigBee, IEEE 802.11, IEEE 802.15, Infrared Data Association (IrDA) protocols, and standards related to any of the foregoing.

In some other or additional implementations, (a) includes: (i) determining a time remaining before stored ephemeris data is no longer current, (ii) comparing the time remaining determined in (i) to an ephemeris data update time threshold, and (iii) requesting updated ephemeris data from the secondary device when the time remaining is less than the ephemeris data update time threshold. In some such implementations, the ephemeris data update time threshold is a time less than 2 hours. In some other or additional implementations, (a) further includes, between (ii) and (iii), (iv) detecting that the secondary device is within communication range.

In some other or additional implementations, the secondary device obtains updated ephemeris data from a navigation satellite.

In some other or additional implementations, the secondary device obtains updated ephemeris data from an Earth-based organization serving updated ephemeris data.

In some other or additional implementations, (b) includes obtaining X amount of days of ephemeris data and X is a number between 0 and 30.

In some other or additional implementations, (a) includes determining that a more recently updated version of the ephemeris data stored on the worn biometric monitoring device is available and (b) includes obtaining the more recently updated version of the ephemeris data via the short-range, low-power communication from the secondary device associated with the worn biometric monitoring device.

In some implementations, a method of determining a global position of a worn biometric monitoring device may be provided. The method may include: (a) repeatedly and automatically syncing the worn biometric monitoring device with a secondary device associated with the worn biometric monitoring device, wherein the syncing includes providing the worn biometric monitoring device with current ephemeris data from the secondary device using a wireless short-range, low-power communication protocol.

In some such implementations, the method may further include: (b) determining that a global position of the worn biometric monitoring device should be calculated and (c) calculating the global position of the worn biometric monitoring device using the ephemeris data obtained in (a), wherein at least some of the syncing operations are conducted when the worn biometric monitoring device is not determining the global position of the worn biometric device.

In some other or additional implementations, each syncing may include: (i) determining an elapsed time from when the ephemeris data was last updated, (ii) comparing the elapsed time with a sync time threshold, (iii) determining that the elapsed time exceeds the sync time threshold, and (iv) obtaining updated ephemeris data from the secondary device. In some such implementations, the sync time threshold is between every 5 minutes to every 2 hours.

In some other or additional implementations, the worn biometric monitoring device is regularly synced with the secondary device according to a schedule. In some such implementations, the schedule is a time schedule according to the time of day. In some other or additional implementations, the method my further include determining the schedule by monitoring a pattern of interaction of a user with the biometric monitoring device.

In some other or additional implementations, the method further includes (d) determining, before (a), that the worn biometric monitoring device is associated with the secondary device.

In some implementations, a wearable biometric monitoring device may be provided. The wearable biometric monitoring device including communication circuitry, the communication circuitry configured to receive ephemeris data from a secondary device associated with the wearable biometric monitoring device via a wireless short-range, low-power communication protocol and output the ephemeris data to a controller, and the controller including one or more processors and a memory, wherein the one or more processors, the memory, and the communication circuitry, are communicatively connected and the memory is configured to store ephemeris data and program instructions for controlling the one or more processors to: (a) repeatedly and automatically sync the wearable biometric monitoring device with the secondary device, wherein the sync includes obtaining current ephemeris data from the secondary device, (b) determine that a global position of the wearable biometric monitoring device should be calculated, and (c) calculate the global position using the current ephemeris data obtained in (a), wherein at least some of the syncing is conducted when the wearable biometric monitoring device is not determining the global position of the wearable biometric monitoring device.

In some such implementations, each sync obtained in (a) includes: (i) determining an elapsed time from when the ephemeris data was last updated, (ii) comparing the elapsed time with a sync time threshold, (iii) determining that the elapsed time exceeds the sync time threshold, and (iv) obtaining updated ephemeris data from the secondary device. In some such implementations, the sync time threshold is between every 5 minutes to every 2 hours.

In some other or additional implementations, the wearable biometric monitoring device is regularly synced with the secondary device according to a schedule. In some such implementations, the schedule is a time schedule according to the time of day. In some other or additional implementations, the schedule is determined by monitoring a pattern of interaction of a user with the biometric monitoring device.

In some other or additional implementations, the memory stores further program instructions for controlling the one or more processors to: (d) determine, before (a), that the worn biometric monitoring device is associated with the secondary device.

In some implementations, a method of determining a global position of a worn biometric monitoring device may be provided. The method including: (a) obtaining position fixing data by interacting with a navigation satellite, (b) providing the position fixing data to an associated secondary device so that the associated secondary device can calculate a global position of the worn biometric monitoring device, wherein the worn biometric monitoring device provides the position fixing data to the associated secondary device via a wireless short-range, low-power communication protocol, and (c) receiving the global position from the secondary device.

In some such implementations, the worn biometric monitoring device may include a navigation data receiver.

In some other or additional implementations, the worn biometric monitoring device includes a navigation data receiver and the interacting with the navigation satellite includes receiving the position fixing data from the navigation satellite via the navigation data receiver using wireless communication.

In some other or additional implementations the method may further include: (d) storing the position fixing data in a memory after (a) and before (b).

In some other or additional implementations the method may further include: (e) determining, before (a), that the global position of the worn biometric monitoring device should be calculated.

In some other or additional implementations the short-range, low-power communication protocol includes protocols selected from the group consisting of Bluetooth, ANT, near field communication (NFC), ZigBee, IEEE 802.11, IEEE 802.15, Infrared Data Association (IrDA) protocols, and standards related to any of the foregoing.

In some implementations, a method of determining a global position of a worn biometric monitoring device may be provided. The method may include: (a) obtaining position fixing data by interacting with a navigation satellite, (b) providing the position fixing data to a associated secondary device via a wireless short-range, low-power communication protocol, and (c) calculating the global position from the position fixing data with the associated secondary device.

In some such implementations, the method may further include (d) displaying a graphical representation of the global position on the associated secondary device.

In some other or additional implementations, the method may further include (e) communicating the global position from the associated secondary device to a tertiary device.

In some implementations, a wearable biometric monitoring device may be provided. The wearable biometric monitoring device may include: communication circuitry, the communication circuitry configured to output data to a secondary device associated with the wearable biometric monitoring device via a wireless short-range, low-power communication protocol and receive a global position from the secondary device, a navigation data receiver, the navigation data receiver configured to receive the position fixing data from a navigation satellite and output the position fixing data to the controller, and the controller including one or more processors and a memory, wherein the one or more processors, the memory, the communication circuitry, and the navigation data receiver are communicatively connected and the memory is configured to store program instructions for controlling the one or more processors to: (a) obtain the position fixing data from the navigation satellite, (b) provide the position fixing data to the associated secondary device via the communication circuitry so that the secondary device can calculate a global position of the wearable biometric monitoring device, and (c) receive the global position from the secondary device.

In some such implementations, the memory may store further program instructions for controlling the one or more processors to (d) store the position fixing data in the memory after (a) and before (b).

In some other or additional implementations, the memory may store further program instructions for controlling the one or more processors to (e) determine, before (a), that the global position of the wearable biometric monitoring device should be calculated.

In some other or additional implementations, the short-range, low-power communication protocol may include protocols selected from the group of Bluetooth, ANT, near field communication (NFC), ZigBee, IEEE 802.11, IEEE 802.15, Infrared Data Association (IrDA) protocols, and standards related to any of the foregoing.

In some implementations, a method of determining a global position of a worn biometric monitoring device, including a navigation data receiver and a motion-detecting sensor, may be provided. The method may include: (a) determining that the worn biometric monitoring device has moved after being substantially stationary and (b) in response to determining that the worn biometric monitoring device has moved, obtaining updated ephemeris data via a wireless short-range, low-power communication protocol from a secondary device associated with the worn biometric monitoring device.

In some such implementations, the method may further include: (c) determining that a global position of the worn biometric monitoring device should be calculated and (d) calculating the global position of the worn biometric monitoring device using the ephemeris data obtained in (b).

In some other or additional implementations, the motion-detecting sensor is a sensor selected from the group consisting of: an accelerometer, a gyroscope, a magnetometer, an altitude sensor, a user interface, an environmental sensor, a light sensor, a pedometer, and a global position sensor.

In some other or additional implementations, the motion-detecting sensor is an accelerometer configured to detect acceleration of the worn biometric monitoring device and determining that the worn biometric monitoring device has moved in (a) includes detecting an acceleration greater than a threshold value of acceleration. In some such implementations, the threshold value of acceleration is acceleration of the worn biometric monitoring device greater than 3 m/s$^2$.

In some other or additional implementations, the motion-detecting sensor is a gyroscope configured to detect a change in orientation of the worn biometric monitoring device and determining that the worn biometric monitoring device has moved in (a) includes detecting a change in orientation of the worn biometric monitoring device.

In some other or additional implementations, the motion-detecting sensor is an altitude sensor configured to detect a change in altitude of the worn biometric monitoring device and determining that the worn biometric monitoring device has moved in (a) includes detecting a change in altitude of the worn biometric monitoring device.

In some other or additional implementations, the motion-detecting sensor is a light sensor configured to detect UV light and determining that the worn biometric monitoring device has moved in (a) includes sensing, with the light sensor, the presence of UV light.

In some other or additional implementations, (a) is determined by the associated secondary device.

In some implementations, a method of determining a global position of a worn biometric monitoring device including a navigation data receiver and a user interface may be provided. The method including: (a) determining that a user is interacting with the user interface and (b) in response to determining that the user is interacting with the user interface, obtaining updated ephemeris data via a wireless short-range, low-power communication protocol from a secondary device associated with the worn biometric monitoring device.

In some such implementations, the method further includes: (c) determining that a global position of the worn biometric monitoring device should be calculated and (d) calculating the global position of the worn biometric monitoring device using the ephemeris data obtained in (b).

In some implementations, a method of determining a global position of a worn biometric monitoring device including a navigation data receiver, a motion-detecting sensor, a battery, and a controller may be provided. The method including: (a) determining that an ephemeris data threshold update condition is met and (b) in response to determining that the ephemeris data threshold update condition is met, obtaining updated ephemeris data via a wireless short-range, low-power communication protocol from a secondary device associated with the worn biometric monitoring device.

In some such implementations, the method may further include: (c) determining that a global position of the worn biometric monitoring device should be calculated and (d) calculating the global position of the worn biometric monitoring device using the ephemeris data obtained in (b).

In some other or additional implementations, the ephemeris data threshold update condition is one or more of: (i) detecting a wireless connection with the secondary device exceeding a threshold connection strength, (ii) determining that the battery has a battery charge level exceeding a battery charge threshold, (iii) determining that the controller has a spare processing ability exceeding a threshold processing ability, and (iv) determining that the worn biometric monitoring device is in a stationary state.

In some other or additional implementation, (a) is determined by the associated secondary device.

In some implementations, a wearable biometric monitoring device may be provided. The wearable biometric monitoring device may include a motion-detecting sensor, the motion-detecting sensor configured to detect acceleration of the wearable biometric monitoring device and output motion data to a controller, communication circuitry, the communication circuitry configured to receive data from a secondary device associated with the biometric monitoring device via a wireless short-range, low-power communication protocol and output data to the controller, and the controller with one or more processors and a memory, wherein the one or more processors, the memory, the motion-detecting sensor, and the communication circuitry, are communicatively connected and the memory is configured to store program instructions for controlling the one or more processors to: (a) determine that the wearable biometric monitoring device has moved, (b) in response to the determination that the wearable biometric monitoring device has moved, obtain updated ephemeris data from the secondary device, and (c) calculate a global position of the wearable biometric monitoring device using the ephemeris data obtained in (b).

In some such implementations, the apparatus may further include a motion-detecting sensor selected from the group consisting of: an accelerometer, a gyroscope, a magnetometer, an altitude sensor, a user interface, an environmental sensor, a light sensor, a pedometer, and a global position sensor.

In some other or additional implementations, the apparatus may further include an accelerometer configured to detect acceleration of the wearable biometric monitoring device and output acceleration data to the controller, wherein (a) includes detecting an acceleration greater than a threshold value of acceleration from the acceleration data. In some such implementations, the threshold value of acceleration is acceleration of the worn biometric monitoring device greater than 3 m/s$^2$.

In some other or additional implementations, the apparatus may further include a gyroscope configured to detect a change in orientation of the wearable biometric monitoring device and output orientation data to the controller, wherein (a) includes detecting a change in orientation from the orientation data.

In some other or additional implementation, the apparatus may further include an altitude sensor configured to detect a change in altitude of the wearable biometric monitoring device and output altitude data to the controller, wherein (a) includes detecting a change in altitude from the altitude data.

In some other or additional implementation, the apparatus may further include a light sensor configured to detect UV light and output light data to the controller, wherein (a) includes sensing the presence of UV light from the light data.

In some implementations, a wearable biometric monitoring device may be provided. The wearable biometric monitoring device may include a user interface, the user interface configured to interact with a user, communication circuitry, the communication circuitry configured to receive data from a secondary device associated with the biometric monitoring device via a wireless short-range, low-power communication protocol and output data to the controller, and a controller with one or more processors and a memory, wherein the one or more processors, the memory, the user interface, and the communication circuitry, are communicatively connected and the memory is configured to store program instructions for controlling the one or more processors to: (a) determine that the user is interacting with the user interface, (b) in response to the determination that the user is interacting with the user interface, obtain updated ephemeris data from the secondary device, and (c) calculate a global position of the wearable biometric monitoring device using the ephemeris data obtained in (b).

In some implementations, a wearable biometric monitoring device may be provided. The wearable biometric monitoring device may include a motion-detecting sensor, the motion-detecting sensor configured to detect acceleration of the wearable biometric monitoring device and output motion data to a controller, a battery, the battery configured to provide battery power to the wearable biometric monitoring device, communication circuitry, the communication circuitry configured to receive data from a secondary device associated with the wearable biometric monitoring device via a wireless short-range, low-power communication protocol and output data to the controller, and the controller with one or more processors and a memory, wherein the one or more processors, the memory, the motion-detecting sensor, and the communication circuitry, are communicatively connected and the memory is configured to store program instructions for controlling the one or more processors to: (a) determine that an ephemeris data threshold update condition is met, (b) in response to determining that the ephemeris data threshold update condition is met, obtaining updated ephemeris data via a wireless short-range, low-power communication protocol from a secondary device associated with the wearable biometric monitoring device, and (c) calculate a global position of the wearable biometric monitoring device using the updated ephemeris data obtained in (b).

In some such implementations, the ephemeris data threshold update condition may be one or more of: (i) detecting a wireless connection with the secondary device exceeding a threshold connection strength, (ii) determining that the battery has a battery charge level exceeding a battery charge threshold, (iii) determining that the controller has spare processing ability exceeding a threshold processing ability, and (iv) determining that the wearable biometric monitoring device is stationary.

In some implementations, a wearable biometric monitoring device may be provided. The wearable biometric monitoring device may include a user interface, the user interface configured to interact with a user, communication circuitry, the communication circuitry configured to receive data from a portable camera associated with the biometric monitoring device and output the data to a controller, and the controller with one or more processors and a memory, wherein the one or more processors, the memory, the user interface, and the communication circuitry, are communicatively connected and the memory is configured to store program instructions for controlling the one or more processors to wirelessly interact with the portable camera.

In some such implementations, the communication circuitry is further configured to communicate data to the portable camera via a short-range, low-power communication protocol.

In some other or additional implementations, wirelessly interacting with the portable camera may include wirelessly receiving video data from the portable camera. In some such implementations, the user interface is a digital display, the controller is further configured to display the video data from the portable camera on the user interface, and the video data from the portable camera is communicated from the portable camera to the wearable biometric monitoring device via the communication circuitry. In some other or additional implementations, the video data from the portable camera is current video data recorded by the portable camera and communicated directly to the wearable biometric monitoring device.

In some other or additional implementations, the video data from the portable camera is video data stored on a memory on the portable camera prior to the wearable biometric monitoring device receiving the video data from the portable camera.

In some other or additional implementations, wirelessly interacting with the portable camera includes starting a recording by the portable camera and stopping a recording by the portable camera.

In some implementations, a wearable biometric monitoring device may be provided. The wearable biometric monitoring device may include a first housing including a controller, communication circuitry, the communication circuitry configured to receive data from a secondary device associated with the wearable biometric monitoring device via a wireless short-range, low-power communication protocol and output the data to the controller, and a second housing configured to attach to the first housing, wherein the second housing includes at least a portion of the communication circuitry.

In some such implementations, at least a portion of the communication circuitry included in the second housing is configured to electrically connect to the controller when the second housing is attached to the first housing. In some implementations, the first housing includes a metallic portion electrically connected to the controller and the metallic portion is configured to electrically connect to the at least a portion of the communication circuitry included in the second housing when the second housing is attached to the first housing. In some other or additional implementations, the first housing includes electrically conductive content electrically connected to the controller and the electrically conductive content is configured to electrically connect to the at least a portion of the communication circuitry included in the second housing when the second housing is attached to the first housing.

These and other features of the disclosed embodiments will be described in more detail below.

BRIEF DESCRIPTION OF THE DRAWINGS

The various embodiments disclosed herein are illustrated by way of example, and not by way of limitation, in the figures of the accompanying drawings and in which like reference numerals refer to similar elements and in which.

INTRODUCTION

Figure 10:
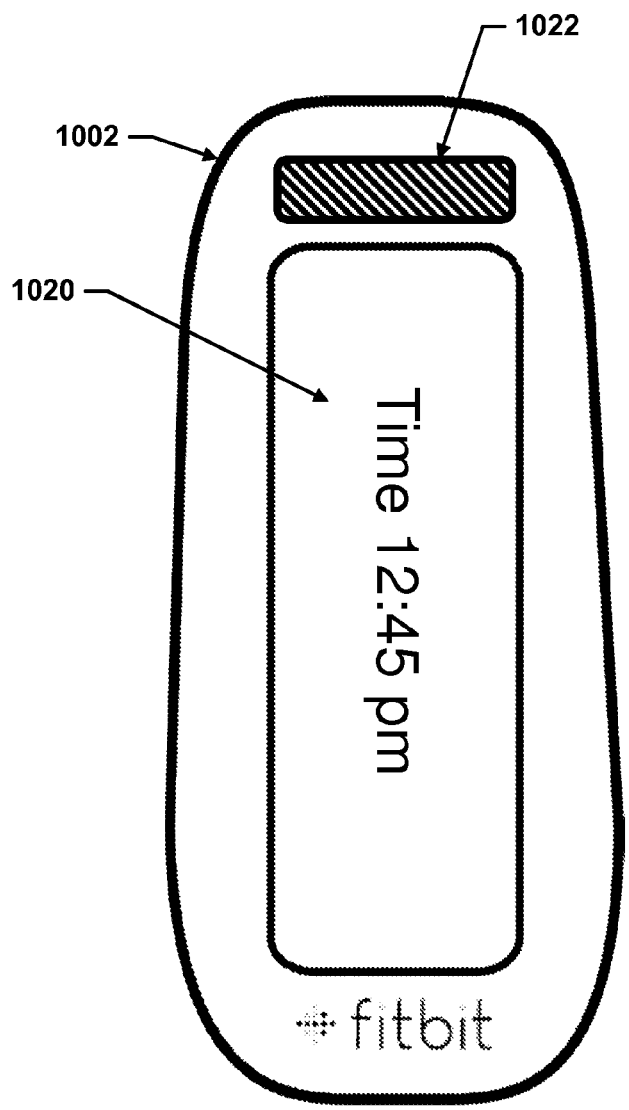
FIG. 10 shows an example of a portable biometric monitoring device having a button and a display.

Portable biometric monitoring devices according to embodiments described herein have shapes and sizes adapted for coupling to (e.g., secured to, worn, borne by, etc.) the body or clothing of a user. Examples of portable biometric monitoring devices are shown in FIG. 10 and II. The devices collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device then transmits data representative of the user's step count to an account on a web service (e.g., fitbit.com), computer, mobile phone, or health station where the data may be stored, processed, and visualized by the user. Indeed, the device may measure or calculate a plurality of other physiological metrics in addition to, or in place of, the user's step count. These include, but are not limited to, energy expenditure (e.g., calorie burn), floors climbed and/or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (e.g., medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive. Further embodiments and implementations of sensor devices can be found in U.S. patent application Ser. No. 13/156,304 (U.S. Patent Publication 2012-0083715 A1), titled "Portable Biometric Monitoring Devices and Methods of Operating Same" filed Jun. 8, 2011 which is entirely incorporated herein by reference.

DETAILED DESCRIPTION

Implementation of Location Sensors in Portable Biometric Monitoring and Other Devices There are many valuable biometrics which can be determined through the use of location sensors such as Global Positioning System (GPS), Global Navigation Satellite System (GLONASS), and cell phone trilateration. However, location sensors can present a variety of problems in terms of user interaction and device design in portable biometric monitoring devices. If the device has not been used for a period of time (generally longer than about a minute) it does not have enough information to know where to start its search for satellites. The amount of time it takes for a location sensor to find its location after having not been used for a period of time is called the "time to first fix" or TTFF. Many location sensors have a TTFF which is unacceptably long from a user's perspective. For example, if users would like to go for a bike ride, they may have to wait multiple minutes after turning on their location sensitive device before starting their ride to get location data.

Another issue associated with the use of Global Navigation Satellite System (GNSS) equipped portable biometric monitoring devices is their power consumption. Multiple inventions discussed herein describe how power consumption of GNSS sensors can be greatly reduced by intelligently duty cycling the GNSS sensor or sensors. Additional or alternative power savings can be achieved by using a remote computing device to do some or all of the processing required to calculate locations.

Some techniques described herein which aid a GNSS sensor are referred to as "Assisted-GPS" or "A-GPS." A-GPS can be split up into two sub categories. In Mobile Station Based A-GPS, the location sensitive device (or "mobile station") acquires information from sources other than GNSS satellites to aid in the determination of its location. The location sensitive device may be a wearable biometric monitoring device. The wearable biometric monitoring device may include a navigation data receiver. The navigation data receiver may be a GPS receiver or similar component which may receive position fixing data. The location of the device is calculated from the position fixing data on the wearable biometric monitoring device itself.

In Mobile Station Assisted A-GPS, some or all of the processing required to calculate the location sensitive device's location is performed on one or more secondary devices (e.g. a remote server in wireless communication with the location sensitive device).

Various examples below describe a navigation system employing one or more satellites that transmit ephemeris and/or position fixing data. For the purposes of simplicity, the examples refer to a navigation satellite, but each example may also be implemented with multiple navigation satellites, one or more of which communicate ephemeris data and/or position fixing data. The same navigation satellite may communicate both ephemeris data and position fixing data, or ephemeris data and position fixing data may be communicated through separate navigation satellites. The navigation satellites may be satellites in a GPS system, or it may be navigation satellites in another navigation satellite system such as the Russian Global Navigation Satellite System, the European Union Compass system, the Indian Regional Navigational Satellite System, or the Chinese Compass navigation system.

Assisted-GPS—Mobile Station Based

In one embodiment, additional data may be automatically provided to the location sensitive device to enable it to have a shorter TTFF. For example, precalculated GNSS ephemeris data may be sent to the location sensitive device through a wired or wireless connection. Having current ephemeris data available can increase the accuracy of the GNSS as well as reduce the TTFF. This ephemeris data is generally wirelessly communicated from a server hosted by commercial or public sources such as Mediatek, CSR, and The National Geodetic Survey (NGS) of National Oceanic and Atmospheric Administration. However, the ephemeris data is only valid for a certain period of time. Depending on the type of data downloaded, it may be valid for a period of time varying from seconds to days. In one aspect of this disclosure, ephemeris data is automatically uploaded to the location sensitive device.

Figure 1:
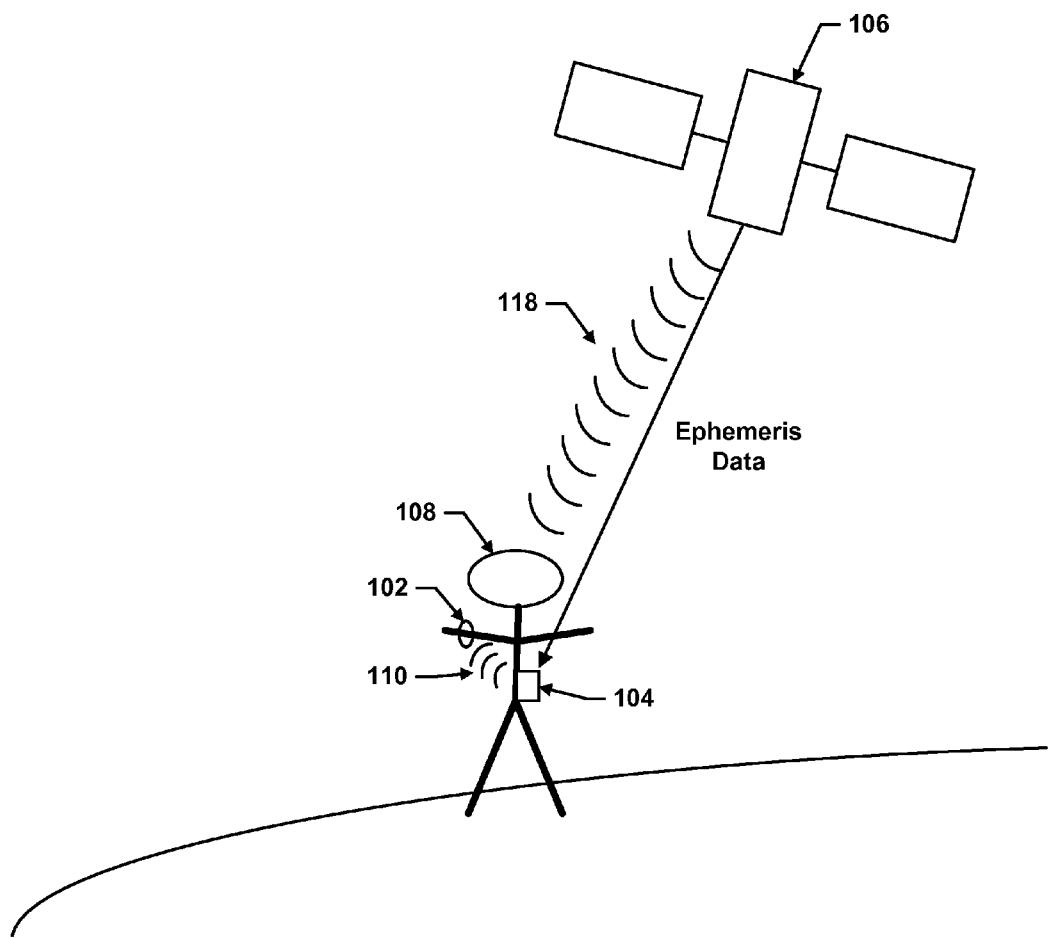
FIG. 1 shows an example configuration of a mobile station based Assisted-GPS of a worn biometric monitoring device for obtaining ephemeris data from a paired secondary device.

FIG. 1 shows an example configuration of a mobile station based Assisted-GPS of a worn biometric monitoring device for obtaining ephemeris data from a paired secondary device. FIG. 1, includes a biometric tracking device 102, a secondary device 104, a navigation satellite 106, and a user 108. The user 108 wears the biometric tracking device 102.

In FIG. 1, ephemeris data is transmitted from the navigation satellite 106 to the secondary device 104. The secondary device may be a computing device such as a smartphone, tablet, or laptop. The secondary device may be any device associated with the biometric tracking device, including secondary devices paired with the biometric tracking device. The secondary device may be associated with the biometric tracking device through Bluetooth, through a WiFi connection, or through other types of communications pairing. In other embodiments, the secondary device is a computing device connected to an ephemeris server. The secondary device may automatically download the ephemeris data from the navigation satellite or the ephemeris server. In some cases, a dongle (e.g., a USB dongle) may be connected to the secondary device to enable the secondary device to wirelessly communicate with the worn biometric monitoring device. The secondary device may then wirelessly communicate the ephemeris device to the worn biometric monitoring device.

When the worn biometric monitoring device is within wireless communication range of the secondary device 104 (or alternatively connected to the secondary device through a wired connection), a portion or all of the ephemeris data may be downloaded to the worn biometric monitoring device 102 through a transmission 110. The worn biometric monitoring device 102 may download the current ephemeris data from the secondary device 104 via a wireless short-range, low-power communication protocol. A wireless short-range, low-power communication protocol may be any communication protocol designed to communicate data over short distances, such as distances less than 200 meters, from fixed and mobile devices and personal area networks. Wireless short-range, low-power communication protocols may include protocols such as Bluetooth, ANT, near field communication (NFC), ZigBee, IEEE 802.11, IEEE 802.15, Infrared Data Association (IrDA) protocols, and other related communication protocols. This will ensure that the ephemeris data is up to date, allowing a quick TTFF from a cold start.

Using the ephemeris data, the worn biometric tracking device A02 may then obtain position fixing data 118 from the navigation satellite 106 to calculate the global position of the worn biometric tracking device 102. The worn biometric tracking device 102 may include a GPS receiver or other navigation data receiver to receive the position fixing data 118. The position fixing data may be any data which allows a processor to calculate the global position of the worn biometric tracking device 102. The position fixing data 118 may be timed signals sent by GPS satellites orbiting the earth. The timed signals may include data relating to the time the message was transmitted and the position of the satellite at the time of message transmission. The position fixing data 118 is then utilized to calculate the global position of the worn biometric tracking device 102. The global position may be calculated from the position fixing data using methods such as the Least Squares Method or Bancroft's Method.

Figure 2:
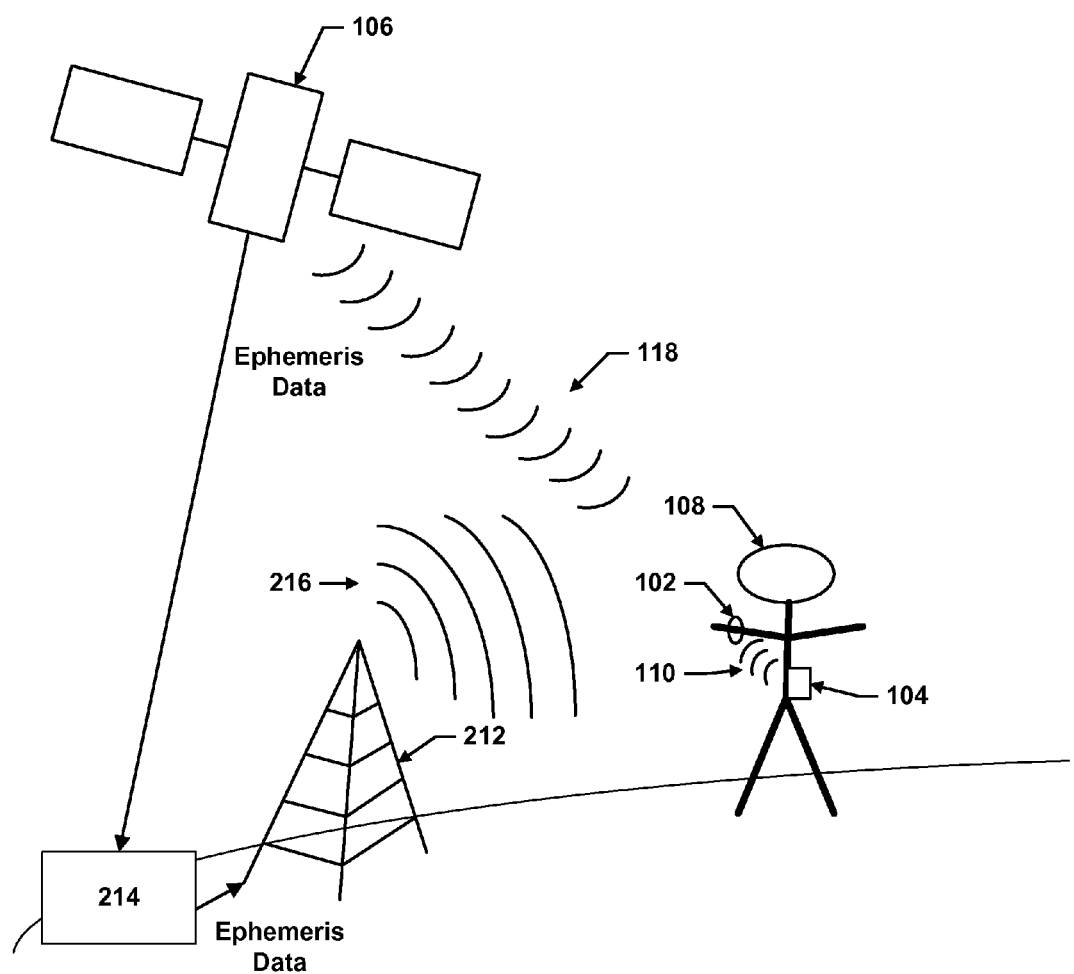
FIG. 2 shows a further example configuration of a mobile station based Assisted-GPS of a worn biometric monitoring device for obtaining ephemeris data from a paired secondary device.

FIG. 2 shows a further example configuration of a mobile station based Assisted-GPS of a worn biometric monitoring device for obtaining ephemeris data from a paired secondary device. FIG. 2 includes the biometric tracking device 102, the secondary device 104, the navigation satellite 106, the user 108, the cellphone tower 212, and the A-GPS server 214.

In FIG. 2, ephemeris data is transmitted from the navigation satellite 106 to the A-GPS server 214. Alternatively, A-GPS server 214 may obtain ephemeris data from another source, such as servers hosted by public or private organizations or the ephemeris data may be preloaded from a different source. The A-GPS server 214 may be a server hosted by commercial or public sources such as Mediatek, CSR, and The National Geodetic Survey (NGS) of National Oceanic and Atmospheric Administration. The A-GPS server 214 may communicate the ephemeris data to the cellphone tower 212. The cellphone tower 212 may then communicate the ephemeris data to the secondary device 104 through cell tower signal 216. The cell tower signal 216 may be a signal that carries the ephemeris data through a communication protocol such as 4G, 3G, LTE, GPRS, HSDPA, EV-DO, WiMax, or other protocol.

The secondary device 104 receives the ephemeris data from the cellphone tower 212 and then transmits the ephemeris data to the worn biometric monitoring device 102 in a manner similar to how the secondary device 104 transmits ephemeris data to the worn biometric monitoring device 102 in FIG. 1. Using the ephemeris data, the worn biometric tracking device A02 may then obtain position fixing data 118 from the navigation satellite 106 to calculate the global position of the worn biometric tracking device 102.

In some embodiments, the secondary device may serve as a "hotspot" where any compatible location sensitive device (e.g., a biometric monitoring device) may be able to download ephemeris data. Alternatively, the secondary device may only allow one specific location sensitive device or a set of location sensitive devices to download ephemeris data. The set of devices which can download ephemeris data may be selected by, e.g., the user of the secondary device, the entity supplying biometric monitoring devices, or the manager of the ephemeris data server for example.

Figure 3:
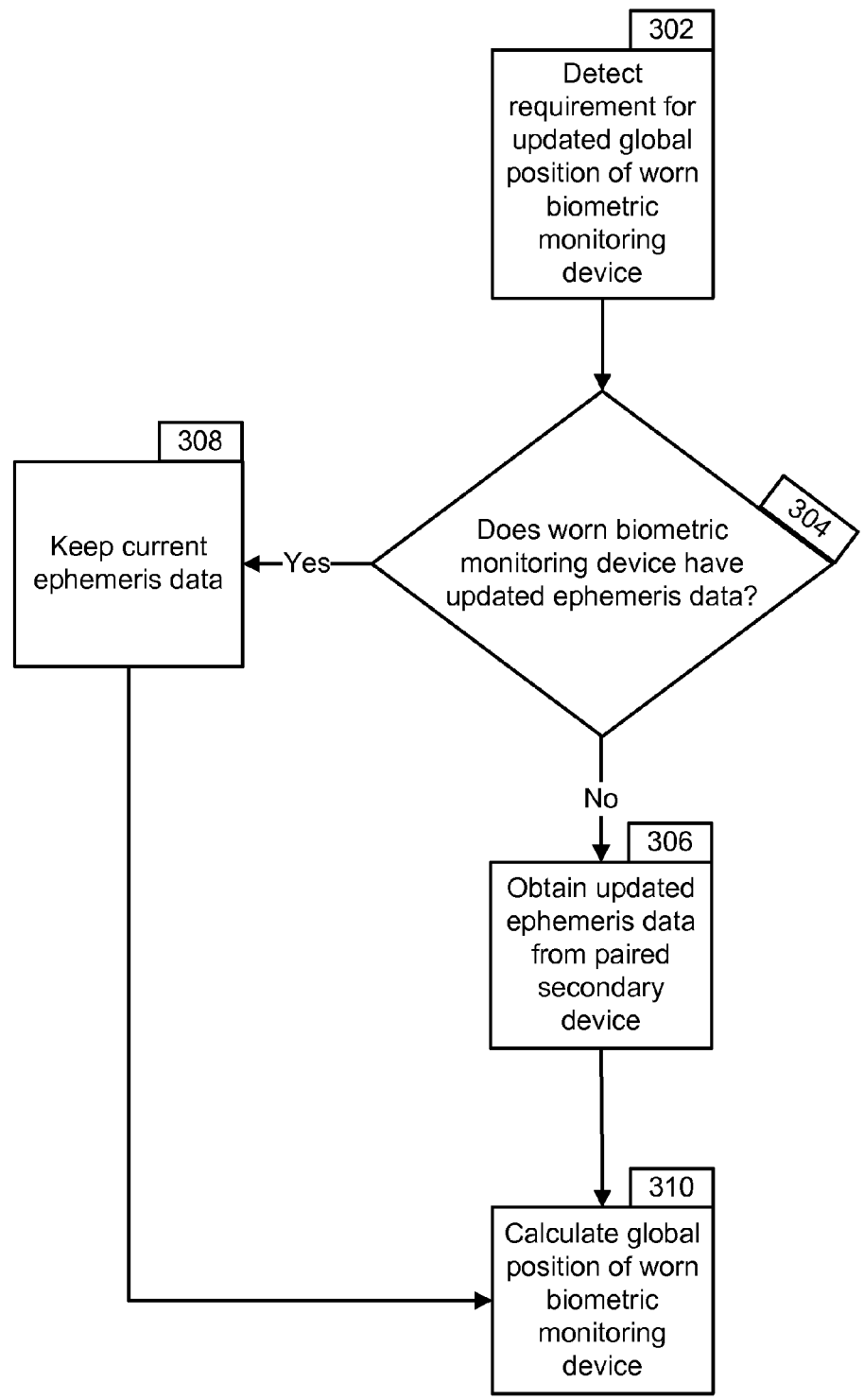
FIG. 3 shows a flow diagram detailing an example of updating ephemeris data through a mobile station based Assisted-GPS for a biometric monitoring device.

FIG. 3 shows a flow diagram detailing an example of updating ephemeris data through a mobile station based Assisted-GPS for a biometric monitoring device. FIG. 3 illustrates a rule to determine when to update the ephemeris data through detecting whether the ephemeris data is up to date.

In block 302, the requirement for an updated global position of the biometric monitoring device is detected. The requirement for the updated global position may be determined through any one or combination of the rules outlined below for updating ephemeris data. Alternatively, the requirement for the updated global position of the biometric monitoring device may be determined through user interaction with the biometric tracking, such as the user activating certain tracking modes, or through algorithms to determine when the updated global position is needed, such as algorithms determining movement of the biometric tracking device or algorithms for updating the global position of the biometric tracking device according to a set timetable.

In block 304, a determination is made of whether the biometric monitoring device possesses updated ephemeris data. The ephemeris data may be determined to be updated by comparing the time remaining on the validity of the ephemeris data, through determining the last update of the ephemeris data, through determining whether the ephemeris data is currently valid, or through other determinations. If the ephemeris data is determined to be updated, the ephemeris data is then kept, as in block 308, and a global position of the biometric monitoring device is calculated in block 310 utilizing the current updated ephemeris.

If the ephemeris data is determined to be out of date in block 304, then updated ephemeris data is obtained from the paired secondary device in block 306. The biometric tracking device may obtain updated ephemeris data from the paired secondary device in a manner similar to the manner outlined in FIGS. 1 and 2. After updated ephemeris data is obtained from the paired secondary device, the global position of the biometric monitoring device is calculated from the updated ephemeris data in block 310.

Rules may determine when to download the ephemeris data from the server and/or when to upload the ephemeris data to the biometric monitoring device. Rules may also determine which ephemeris data source and what specific ephemeris data file should be downloaded from the server (e.g. from NGS final, NGS Rapid, or Jet Propulsion Laboratory (JPS) GDGPS ephemeris sources as well as which specific A-GPS protocol to download, such as 3gpp, Open Mobile Alliance, Secure User Plane Location V1.0, and Secure User Plane Location V2.0). Similarly, rules may determine what specific ephemeris data is uploaded to the biometric monitoring device. For example, there may be a rule to determine whether to upload all currently available ephemeris data or upload only a portion of currently available ephemeris data. Ephemeris data is typically provided in time increments such as the next hour, day, 10 days, 30 days, etc. In one implementation, a rule determines whether to upload all 30 days of the available ephemeris data to the biometric monitoring device or only a portion, such as 5 days, of the ephemeris data to the biometric monitoring device. Apart from determining how much ephemeris data to upload from the secondary device, a rule can determine how much ephemeris data to download from an external source to the secondary device. In various implementations, the secondary device maintains access to significantly more ephemeris data than it uploads to biometric monitoring device at any given time. For example, a secondary device may download 30 days of available ephemeris data, but only upload 5 days of the available ephemeris data to the biometric monitoring device. Also, a rule may also determine that ephemeris data for only a specific subset satellites will be downloaded.

One rule that may be used to determine the above ephemeris download and upload characteristics may be the time remaining before the ephemeris data on the biometric monitoring device is invalid. For example, if the biometric monitoring device only has one day of valid ephemeris data, the biometric monitoring device may obtain updated ephemeris data from a secondary device the next time the secondary device is in communication with the biometric monitoring device. In another example, the biometric monitoring device may determine a time remaining before ephemeris data stored on the biometric monitoring device is no longer valid. If the time remaining is below an update time threshold, the biometric monitoring device may request updated ephemeris data from a secondary device. Update time thresholds may be times less than about 30 days. For example, the biometric monitoring device may have an update time threshold of six hours. If the time remaining is less than six hours, the biometric monitoring device may obtain updated ephemeris data from the secondary device. Other update time thresholds may be a time period between about 1 to 6 hours, about 10 to 24 hours, about 1 to 10 days, or about 20 to 30 days. Generally, the update time threshold may be any time period of about 30 days or less. In another example, the biometric monitoring device has currently valid ephemeris data that it obtained previously but when a rule dictates, it obtains more recently updated versions of the ephemeris data from the secondary device.

Figure 4:
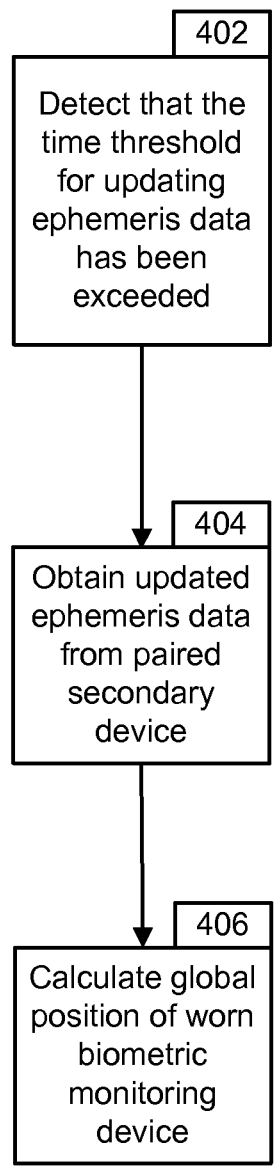
FIG. 4 shows a flow diagram detailing an additional example of updating ephemeris data through a mobile station based Assisted-GPS for a biometric monitoring device.

FIG. 4 shows a flow diagram detailing an additional example of updating ephemeris data through a mobile station based Assisted-GPS for a biometric monitoring device. FIG. 4 illustrates a rule to determine when to update the ephemeris data based on a time threshold.

In block 402 (which may correspond to decision block 304 of FIG. 3), the biometric tracking device or the secondary device detects that the time threshold for updating the ephemeris data has been exceeded. The time threshold may be a threshold determining when the ephemeris data has been previously updated. For example, if it is determined that the ephemeris data was last updated more than 2 hours previously and the time threshold is 2 hours, then it may be determined that the time threshold has been exceeded.

Once the time threshold has been determined to be exceeded, updated ephemeris data is obtained from a secondary device (e.g., a secondary device paired with the biometric monitoring device) in block 404. The updated ephemeris data is obtained from the paired secondary device in a manner similar to that outlined in FIGS. 1 and 2. After updated ephemeris data is obtained from the paired secondary device, the global position of the biometric monitoring device is calculated from the updated ephemeris data in block 406.

Another rule that may be used to determine when to upload ephemeris data to the biometric monitoring device or when the biometric monitoring device downloads updated ephemeris data may be based on movement detected by the biometric monitoring device itself and/or movement detected by the secondary device. Movement may be detected by one or more sensors including but not limited to one or more accelerometers, gyroscopes, and or altimeters. For example, if a user drives to a running path, his smartphone may detect that he is moving. The smartphone may then download ephemeris data and/or other A-GPS data and upload it to the biometric monitoring device. Alternatively, the smartphone may not download ephemeris data and/or other A-GPS data and upload until the smartphone has detected that the user has stopped moving or the smartphone may download ephemeris data and/or other A-GPS data when the smartphone detects that the user is moving, but may not upload the data until the smartphone has detected that the user has stopped moving. In another embodiment, the secondary device may detect the global position of the user and, upon detection of movement by the user resembling a user activity such as walking, running, or other forms of exercise, upload the global position of the user detected by the secondary device to the biometric monitoring device to further reduce the TTFF of the biometric monitoring device.

To save power and to avoid interfering with other processes of the biometric monitoring device, a rule may restrict uploading ephemeris data to certain conditions such as (1) detecting a strong connection between the secondary device and the monitoring device, (2) determining that the monitoring device has at least a defined amount of battery charge remaining, and/or (3) determining that the monitoring device is not engaged in another computationally expensive process such as stair counting. As an example, the ephemeris data of the biometric monitoring device may not be updated unless the biometric monitoring device detects that the biometric monitoring device is stationary. The biometric monitoring device may also update the ephemeris data only if the biometric monitoring device has battery life exceeding a minimum battery amount or if the biometric monitoring device is currently consuming less than a defined amount of computational resources.

In another example, if the sensors on the biometric monitoring device (e.g., watch) detects that the user is interacting with the device (e.g., button pushes, motion events, capacitive touch events), picking up the device (e.g., motion events), walking, running, or otherwise being active, the biometric monitoring device may attempt to download ephemeris data from the secondary device (e.g., smartphone). In a further example, if the sensors detect a change in orientation or altitude of the biometric monitoring device or the secondary device, the ephemeris data of the biometric monitoring device may be updated.

In certain embodiments, a threshold movement magnitude may need to be exceeded before the ephemeris data of the biometric monitoring device is updated. For example, a biometric monitoring device may only update the ephemeris data if acceleration greater than about 3 m/s$^2$ is detected by an accelerometer. Other embodiments may only update the ephemeris data if acceleration of between about 1 to 10 m/s$^2$ is detected. Other thresholds may also be used to determine when to download ephemeris data (e.g., a minimum velocity threshold).

Figure 5:
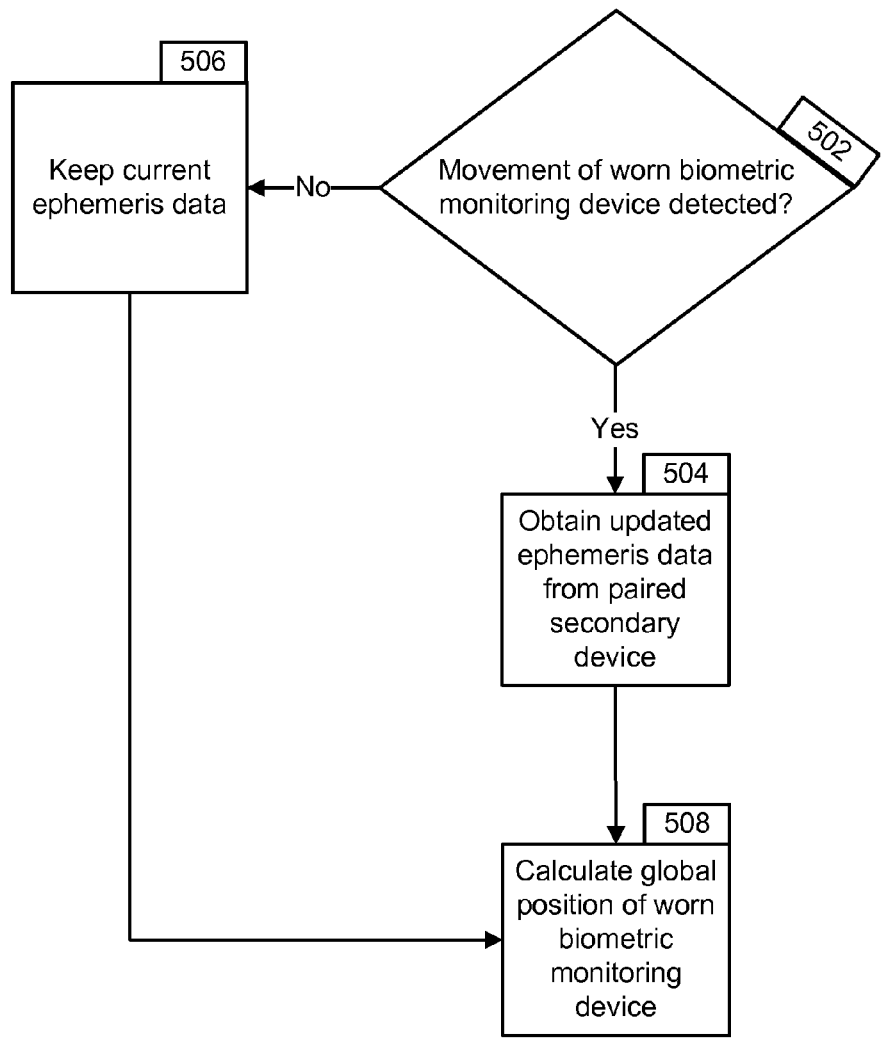
FIG. 5 shows a flow diagram detailing an example of an ephemeris data update algorithm for a mobile station based Assisted-GPS of a biometric monitoring device with a paired secondary device.

FIG. 5 shows a flow diagram detailing an example of an ephemeris data update algorithm for a mobile station based Assisted-GPS of a biometric monitoring device with a paired secondary device. FIG. 5 illustrates a further rule to determine when to update the ephemeris data of the biometric monitoring device.

In block 502, the biometric monitoring device determines whether there is significant movement. As mentioned, movement may be detected by sensors within the biometric monitoring device, such as accelerometers, pedometers, gyroscopes, or magnetometers, or by changes in the physiological data of the user detected by a biometric monitoring sensor.

If no movement is detected, the ephemeris data on the biometric monitoring device is not updated, as in block 506. If movement is detected, the biometric monitoring device then obtains updated ephemeris data from a paired secondary device in block 504.

In block 508, the global position of the biometric monitoring device is calculated. If no movement was detected in block 502, the global position of the biometric monitoring device may be calculated with the un-updated ephemeris data on the biometric monitoring device. If movement was detected in block 502, the global position may be calculated with the updated ephemeris data obtained in block 504. Operation 508 need not directly follow from operation 506 or from operation 504.

Figure 6:
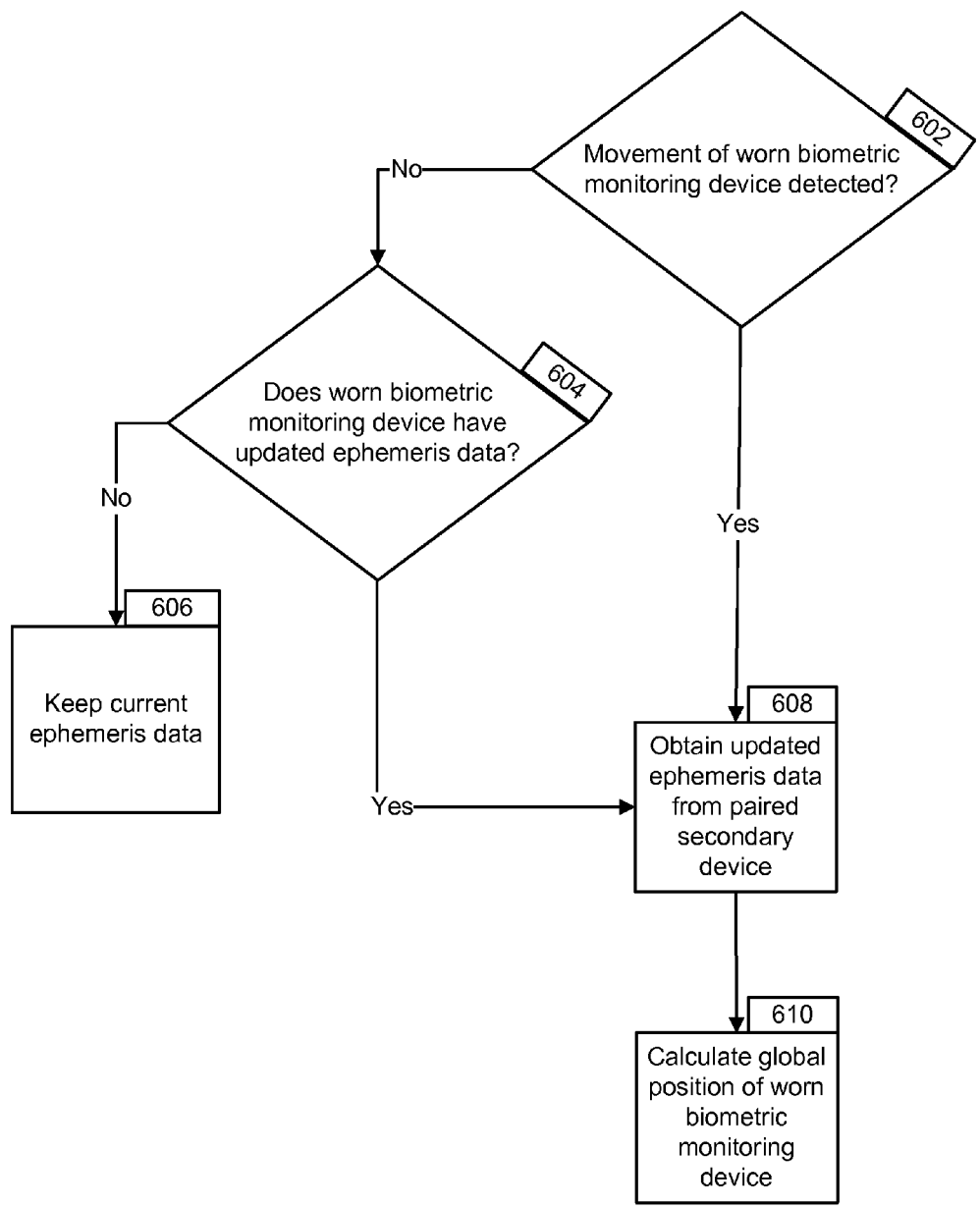
FIG. 6 shows a flow diagram detailing an additional example of an ephemeris data update algorithm for a mobile station based Assisted-GPS of a biometric monitoring device with a paired secondary device.

FIG. 6 shows a flow diagram detailing an additional example of an ephemeris data update algorithm for a mobile station based Assisted-GPS of a biometric monitoring device with a paired secondary device. FIG. 6 may correspond to a combination of the flow diagrams of FIGS. 3 and 5.

In block 602, movement is detected in a manner similar to that in block 502 of FIG. 5. If movement is detected, updated ephemeris data is obtained in block 608 from a paired secondary device. If no movement is detected, then a determination is made whether the biometric monitoring device possesses updated ephemeris data in block 604. The determination made in block 604 may be similar to the determination made in block 304.

If the biometric monitoring device does not possess updated ephemeris data, updated ephemeris data is obtained in block 608 from a paired secondary device. If the biometric monitoring device possesses updated ephemeris data, then the current ephemeris data on the biometric monitoring device is kept.

After updated ephemeris data is obtained, the global position of the biometric monitoring device is calculated with the updated ephemeris data in block 610. The global position of the biometric monitoring device is calculated in a manner similar to that in block 310 of FIG. 3 and block 508 of FIG. 5.

Another rule that may be used to determine when to download ephemeris data or when to turn on the GNSS sensor(s) may be based on the probability that the GNSS sensor(s) can acquire a location fix. For example, it is well known that GPS sensors tend to work better when they are outdoors. Therefore, the biometric monitoring device may only turn on its GPS sensor and/or download ephemeris data when it is outdoors. The biometric monitoring device may be able to determine whether or not it is outdoors based on the difficulty of acquiring one or more satellites signals, based on an ambient light sensor signal and/or a specific light spectrum detected (e.g. UV light detected may indicate that the user is outdoors), based on Wi-Fi or Cell tower multilateration, and/or based on characteristics typical of users or of the user of the biometric monitoring device (e.g. the user may normally be indoors at night when they are sleeping and outdoors during a certain period of time when they commute to work and on the weekends). Additionally, ephemeris data of the biometric monitoring device may only be updated if the biometric monitoring device detects a pairing of sufficient strength with a secondary device. In certain embodiments, when the biometric monitoring device detects a pairing of a predetermined strength with a secondary device, it may automatically download updated ephemeris data from the secondary device.

In some embodiments, learning algorithms may be used to create or adjust the rules. For example, the biometric monitoring device may regularly update ephemeris data by obtaining updated ephemeris data from the paired secondary device. The biometric monitoring device may regularly update the ephemeris data by syncing with the paired secondary device to determine that the ephemeris data of the biometric monitoring device is updated and obtaining updated ephemeris data from the secondary device if the ephemeris data of the biometric monitoring device is not updated. If a user typically syncs their biometric monitoring device with their secondary device every five days, the secondary device may choose to upload an ephemeris file which is valid for seven days, ensuring that the user will have valid ephemeris data before the next sync. Additionally, if the biometric monitoring device detects that a user regularly goes without internet access for a specific amount of days, e.g., about 5 days, the biometric monitoring device may download ephemeris data that is valid for at least the specific amount of days if not more, e.g., about 7 days. Also, if the biometric monitoring device detects that a user regularly goes for a run at a certain time period, the ephemeris data may be updated before the time of the regular run.

GNSS TTFF may also be improved with information from other static or semi-static wireless communication devices including but not limited to cell phone towers and Wi-Fi access points. By using a lookup service such as Skyhook, an accurate location can be quickly determined, especially in urban areas where there are many cell towers and Wi-Fi routers. In some embodiments it may be desirable to not have or use cellular, GNSS and/or Wi-Fi receivers in the biometric monitoring device due to size, power, and cost constraints. However, the biometric monitoring device may be able to take advantage of location sensitive secondary computing devices in communication with the biometric monitoring device. For example, when the biometric monitoring device is within wireless communication range of a secondary device such as a smartphone, the biometric monitoring device may download cellular based, Wi-Fi based, and/or GNSS based location data from the secondary device. Indeed, information from any location determining mechanism on one or more secondary devices may be downloaded to the biometric monitoring device. Such information may aid in accelerating the TTFF of the biometric monitoring device. In such an embodiment, the secondary device may maintain its last known position in memory to communicate to the biometric monitoring device when needed. The smartphone or other secondary device may use Secure User Plane Location (SUPL) to aid in getting a GPS fix. Ephemeris data may also be downloaded from the secondary device as already described.

Assisted-GPS—Mobile Station Assisted

In another embodiment of the present invention, significant power savings and location accuracy can be achieved by offloading the determination of the location of the biometric monitoring device to a remote computing device or server. In this invention, a location sensitive device such as a portable biometric monitoring device acquires a short piece of the position fixing signal from a GNSS satellite. Enough signal is acquired to read a rough timestamp and determine the satellite from which it came from. This raw signal (along with other raw signals from other satellites) is then sent to a remote device (e.g., a secondary computing device) for location calculation. In certain embodiments, the raw signal may be stored on the biometric monitoring device before being sent to the remote device for calculation. In such embodiments, the raw signal may only be sent to the remote device if a condition for sending the raw signal is met. For example, the condition for sending the raw signal may be the detection of an appropriate remote device. The biometric monitoring device may store the raw signal if no remote device is detected. The raw signal may be sent through a short-range, low-power communication protocol, as mentioned above. After the biometric monitoring device sends the raw signal, the remote device, using GPS ephemeris data from one of the sources already discussed, may calculate the location using the raw signal (which does not contain the ephemeris data). This location can then be sent back to the biometric monitoring device soon after calculation or after a condition for sending back the location is met. In other cases, the location may also or alternatively be saved on the remote server. The saved location data (or data derived from this data such as speed) may be presented to the user through an interface other than that of the biometric monitoring device, for example through a web interface.

Figure 7:
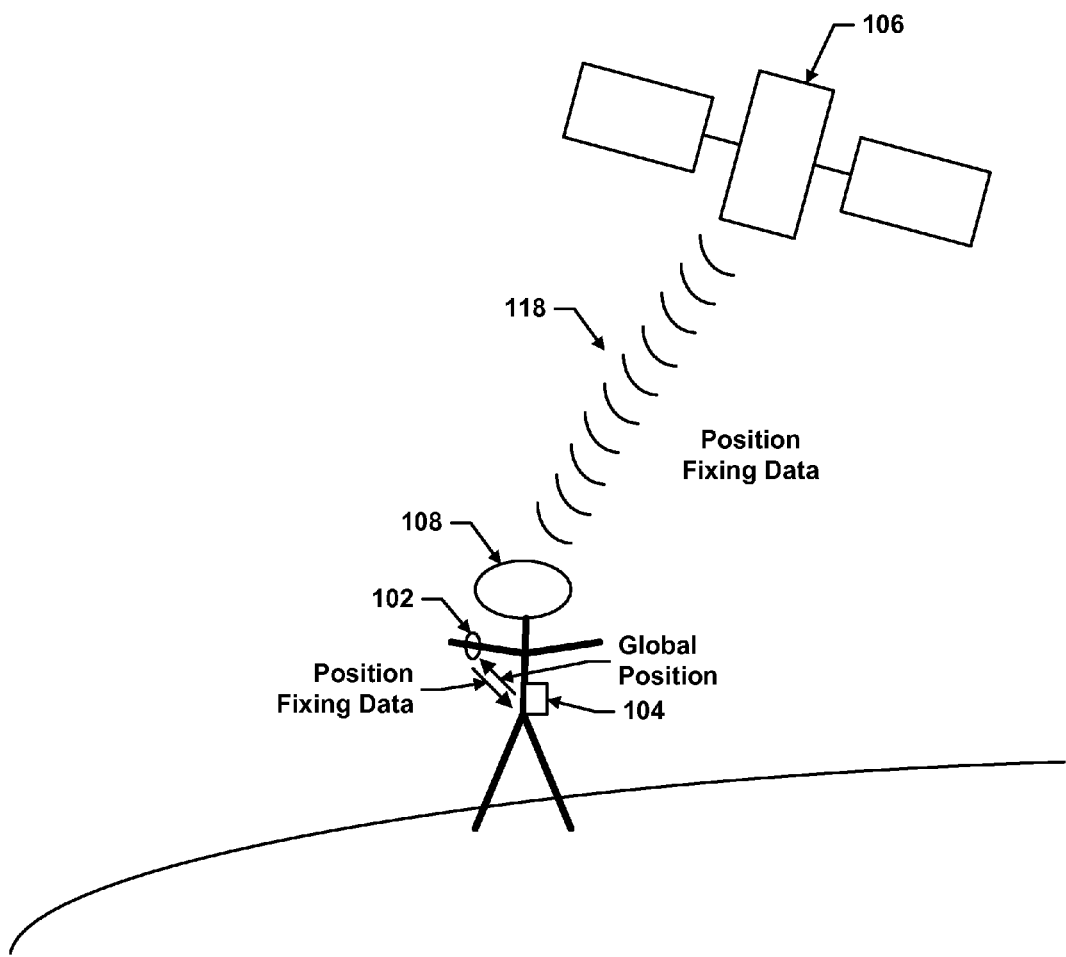
FIG. 7 shows an example configuration of a mobile station assisted calculation of a global position of a worn biometric monitoring device.

FIG. 7 shows an example configuration of a mobile station assisted calculation of a global position of a worn biometric monitoring device. FIG. 7 includes a biometric tracking device 102, a secondary device 104, and a navigation satellite 106.

The navigation satellite 106 communicates position fixing data 118 to the biometric tracking device 102, which is worn by a user 108. Alternatively, the biometric tracking device 102 may not be worn by the user, but may be positioned elsewhere. The position fixing data may be obtained from the navigation satellite in a manner similar to that described in FIGS. 1 and 3. After the biometric tracking device 102 receives the position fixing data, the biometric tracking device 102 communicates the position fixing data to the secondary device 104 via a short-range, low-power communication protocol similar to that described in FIG. 1.

The secondary device 104 calculates the global position from the position fixing data and then communicates the global position to the biometric tracking device 102. The secondary device 104 may communicate the global position to the biometric tracking device 102 via the same short-range, low-power communication protocol as above, or via a different short-range, low-power communication protocol.

Figure 8:
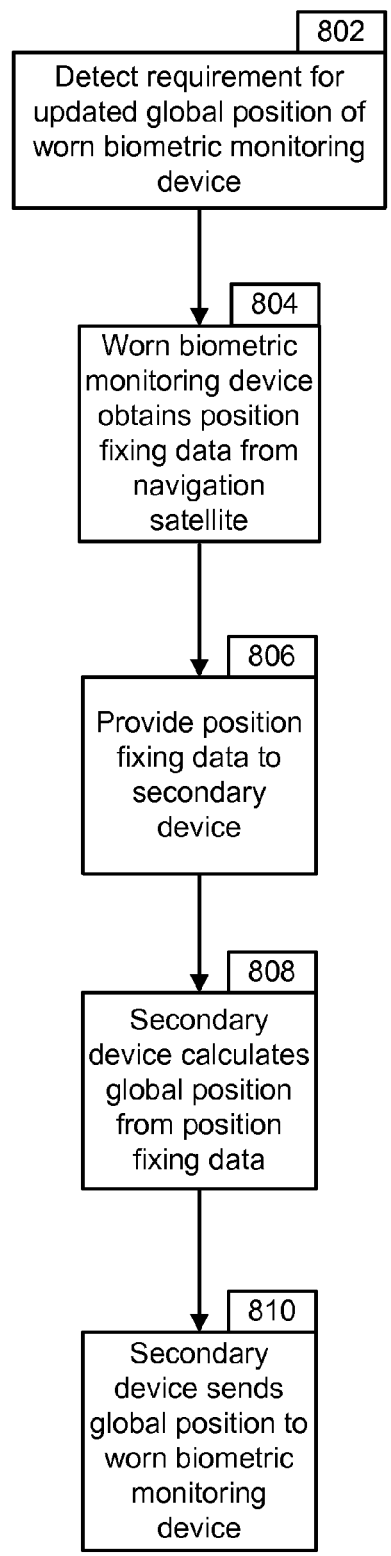
FIG. 8 shows a flow diagram detailing an example of a mobile station assisted calculation of a global position of a biometric monitoring device.

FIG. 8 shows a flow diagram detailing an example of a mobile station assisted calculation of a global position of a biometric monitoring device. In block 802, the requirement for an updated global position of a biometric monitoring device is determined. The requirement may be determined in a manner similar to that in block 302 of FIG. 3.

After the requirement for an updated global position has been determined, the biometric monitoring device obtains position fixing data from a navigation satellite in block 804. The position fixing data may be obtained from the navigation satellite in a manner similar to that described in FIGS. 1 and 3.

After the biometric monitoring device obtains position fixing data, the biometric monitoring device may communicate the position fixing data to the secondary device in block 806 in a manner similar to that described in FIG. 7. After the secondary device receives the position fixing data, the secondary device may calculate the global position from the position fixing data in block 808. The global position may be calculated in a manner similar to that described in FIG. 1.

In block 810, when the secondary device calculates the global position, the secondary device may then communicate the calculated global position to the biometric monitoring device. The secondary device may communicate the global position to the biometric monitoring device in a manner similar to the manner described in FIG. 7. Alternatively, the secondary device may store the global position (for display of information related to the global position by the secondary device) and/or communicate the global position to a tertiary device. The tertiary device may then display information related to the global position. Additionally, other information in addition to the global position, such as the acceleration, velocity, and displacement of the movement of the user as well as other movement data of the user, may also be calculated with mobile station assist.

Assisted-GPS—Inertial Sensor Assisted

In another embodiment, non-GNSS sensors in the location sensitive device may be used to measure movement or the lack thereof. These non-GNSS sensors may include but are not limited to one, multiple or a combination of accelerometers, gyroscope, compasses, and/or magnetometers. Two accelerometers separated by a small distance may be used to measure rotation instead of or in addition to a gyroscope. In one embodiment, one or more sensors may be used to measure when there is no or very little movement of the biometric monitoring device. In the case where no or very little motion is detected since the last GNSS location was acquired, the biometric monitoring device can assume that it is in the same location. This information may be used to speed up the time to first fix.

In the case where movement can be measured by non-GNSS sensors, if the GNSS sensor is turned off or otherwise unable to acquire location data, non-GNSS sensors may be used to update the user's current position. This updated position may subsequently be used to speed up the time to first fix. For example, one or more accelerometers and magnetometers may be used to calculate an updated position using dead reckoning. The next time the GNSS sensor tries to find determine its location, the updated position can be used to improve the time to first fix.

Case-Based Antenna for Location Sensitive Portable Devices

Typically, there is very little space for antennas in portable biometric monitoring devices. The present invention makes use of the space available in the case or attachment mechanisms of the portable biometric monitoring device (e.g. wrist strap, clip case, etc.) by housing an antenna or a portion of the antenna in case or attachment mechanisms. For example, the ground plane of a wrist mounted biometric monitoring device may be incorporated into some or all of the wrist band. Other portions of the antenna, such as a radio frequency radiator, may be incorporated into the wrist band or case as well, or may be incorporated into the biometric monitoring device. In another example, a case for a biometric monitoring device may have contacts which connect the biometric monitoring device to a ground plane formed in the case. In a further example, all components of the antenna may be mounted in a case for a biometric monitoring device. The antenna may then connect to the biometric monitoring device through electrically conductive contact on the biometric monitoring device or through a film of metal on the surface of the biometric monitoring device. Further examples of antennas can be found in U.S. Patent Application No. 61/948,470 titled "Hybrid Radio Frequency/Inductive Loop Antenna," incorporated herein by reference in its entirety. Further examples of cases and attachment mechanisms for a portable biometric monitoring device may be found in U.S. patent application Ser. No. 14/029,764 titled "Wearable Biometric Monitoring Devices, Interchangeable Accessories and Integrated Fastenings to Permit Wear," incorporated herein by reference in its entirety.

Mounted Camera Positioning Aid

It has become common for users to record video or photos of activities such as outdoor recreation. There is high demand for portable cameras which can record video that are small and light enough to be worn on the body, mounted to sports equipment or mounted to other devices including but not limited to vehicles. Despite the convenience of such small mountable cameras over traditional larger cameras, it is often very difficult to position the camera so that they have the appropriate view area. It is also difficult to control (start, stop, pause, etc.) and view recording and playback due to limited user interfaces on the cameras. Control and viewing can also be made more difficult if not impossible when the camera is mounted in certain locations, for example on a helmet.

In one embodiment of the present inventions, a portable biometric monitoring device (e.g. wrist mounted activity tracker) also has capabilities which enables it to wirelessly communicate with one or more cameras to address the difficulties listed above. Namely, the portable biometric monitoring device may wirelessly receive video recorded from the camera to aid in camera positioning and alignment. The portable biometric monitoring device may also be able to wirelessly control the recoding and play back of one or more cameras.

Figure 9:
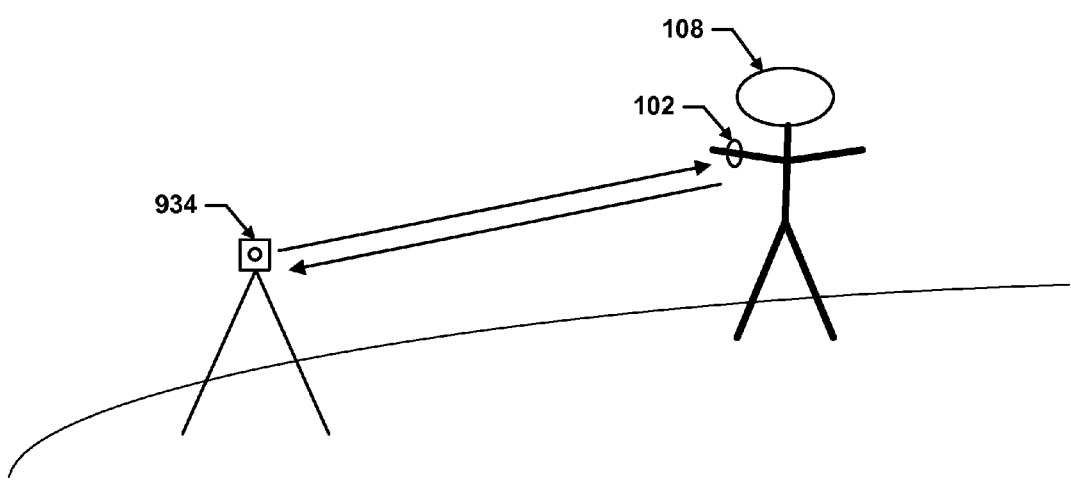
FIG. 9 shows an example configuration of a biometric monitoring device portable camera positioning aid.

For example, one user may be able to position their camera by viewing a live video feed from their camera on their portable biometric monitoring device. They can then start the recording of the camera by interacting with the portable biometric monitoring device. After completing the activity (e.g. getting to the bottom of a ski slope), the user can again interact with their portable biometric monitoring device to stop the recording. The user can then play back their recording or a recording from a friend's camera on the display of their portable biometric monitoring device FIG. 9 shows an example configuration of a biometric monitoring device portable camera positioning aid. FIG. 9 includes a biometric tracking device 102 and a portable camera 934. A user 108 wears the biometric tracking device 102 in FIG. 9.

The biometric tracking device 102 may wirelessly interact with the portable camera 934. The biometric tracking device 102 may, for example, wirelessly receive video or provide instructions to the portable camera 934 as described above. The biometric tracking device 102 may interact with the portable camera 934 through a short-range, low-power communication protocol as described above.

Unified Biometric and Environmental Dashboard

Many biometric and environmental monitoring devices have the capability to send saved data to one or more secondary devices, typically a server. In order to enable users to more easily access and digest this data, it is the goal of the present invention to provide a unified biometric and environmental user interface. This "unified dashboard" user interface would preferably be available through a website and/or application on a computing device such as a smartphone, tablet computer, laptop and/or desktop computer.

The unified dashboard may allow the user to choose what data or information they would like to be presented and how it is presented. For example, the user may be able to choose and organize virtual tiles which display information. Tiles may show biometric data including but not limited to steps taken, distance covered, floors climbing, calories consumed, calories burned as well as environmental data including but not limited to temperature, humidity, air quality (e.g. $CO_2$ concentration, particulates, pollen index, etc.), and predicted weather.

Further embodiments and implementations of multiple data streams (biometric, environmental, etc) can be found in U.S. patent application Ser. No. 14/174,497, titled "Method of Data Stream Synthesis," U.S. patent application Ser. No. 14/178,224, titled "Method of Data Stream Synthesis," and U.S. patent application Ser. No. 14/178,232, titled "Tracking User Physical Activity With Multiple Devices" which are hereby incorporated by reference in their entirety.

Timestream Database

In order to facilitate third party developers of applications running on portable biometric monitoring devices, an accessible database of biometric and/or environmental data may be created. This "timestream" database would enable third party apps to put data such as biometric events (e.g. logging heart rate stat every second, minute, hour, day, week, etc.). As an alternative to the timestream database, a key/value database may be used to store data.

In the context of this disclosure, third party refers to a company or individual which is independent of the company or individual that manages and/or creates the timestream database.

Further embodiments and implementations of multiple data streams relevant to timestream databases can also be found in U.S. Patent Application No. 61/762,210, titled "Method of Data Stream Synthesis" filed Feb. 7, 2013 which is entirely incorporated herein by reference.

Gesture-Based Portable Biometric Monitoring Device Display Control

Portable biometric monitoring devices typically have screens which users can interact with through a variety of input mechanisms including buttons and touchscreens. In some applications, this can yield an unsatisfactory user experience. For example, in the case of a portable biometric monitoring device coupled to the wrist, the user may want to quickly see what time it is on the device without pressing a button. By using accepting user input through physical gestures, the user may be able to intuitively and effortlessly control the display. In this example, the motion of moving the wrist to view the display may cause the display to turn on and/or show the time.

Gesture Sensors

Gestures may be detected through one or more sensors including one or more accelerometers, gyroscopes, EMG sensors, magnetometers, proximity sensors, IR sensors (e.g. to detect IR radiation from a user's face), face and/or eye tracking sensors (e.g. using machine vision), air pressure sensors and strain sensors. Two accelerometers may be used together to detect rotation. One or more accelerometers may measure the displays orientation with respect to gravity, and therefore its orientation (e.g. up, down, sideways, etc.). One or more magnetometers or compass sensors could also be used to measure orientation or detect rotation. In some embodiments one or more of the above sensors may be used together to detect motions or other characteristics which indicate that the user is performing a gesture.

Detected Gestures

One or more gestures may correspond to one or more controls for the display. These gestures may include, but are not limited to one, multiple, or a combination of the follow; looking at the display, facing the display (but not necessarily making eye contact), flexing muscles (e.g. in the wrist, arm or hand), moving or rotating one or more body parts (e.g. moving the wrist in a manner which enables the user to make eye contact with the display). In an embodiment where the device is mounted to the wrist, a "wrist flip" gesture may be detected by measuring the rotation, rotation rate, etc. of the device on the wrist as it moves from an orientation where the display is upside down (relative to the reading direction of the user) to an orientation where the display is right side up. In lieu of or in combination with rotation, the gesture may also be detected through the angle of the device with respect to gravity through, for example, the use of a tilt sensor or accelerometer.

Gesture Controlled Aspects of the Display

One or more gestures may control one or more aspects of the display. In some embodiments, gestures may cause the display to display a certain type of data (e.g. the time). In other embodiments, gestures may affect the responsivity of a touchscreen (e.g. to facilitate user input through the touchscreen, and/or make the device respond to a first touch faster). Gestures may also cause the touchscreen to turn on or off. In other embodiments, gestures may turn the display on or off. In other embodiments, gestures may change the mode of a touchscreen from a low power monochrome mode that is visible without a backlight to a full-color LED backlight display mode. Any characteristic or set of characteristics of the display that can be controlled by software or firmware in the device may be controlled by gestures.

Wrist-Mounted Portable Biometric Monitoring Device Embodiment

In one embodiment illustrative of the use of the present invention, a wrist mounted portable biometric monitoring device may allow a user to control the display through gestures. If the user performs a "wrist flick" gesture where they move and rotate their wrist in a manner which enables them to make eye contact with the display, the display may show the time and/or increase the sensitivity of the touchscreen display.

The "wrist flick" gesture may include, but is not limited to one of the following motions:
  one quick (approximately) 90 degree rotation of the wrist quickly followed by one quick (approximately) 90 degree rotation of the wrist in the opposite direction
  one quick (approximately) 90 degree rotation of the wrist from an orientation where the display is in view of the user to an orientation where the display is not in view of the user quickly followed by one quick (approximately) 90 degree rotation of the wrist in the opposite direction from an orientation where the display is not in view of the user to an orientation where the display is in view of the user
  one quick (approximately) 90 degree rotation of the wrist one quick (approximately) 90 degree rotation of the wrist from an orientation where the display is not in view of the user to an orientation where the display is in view of the user.

The rotation of the gesture may be detected through the use of a variety of sensors already disclosed herein (e.g. through the use of two accelerometers). Orientation of the display may be detected by detecting the orientation of gravity with one or more accelerometers. The display is considered to be "in view of the user" when the user can make eye contact and easily read information presented on the display.

Further embodiments and implementations of gesture based display control can be found in U.S. patent application Ser. No. 14/029,763, titled "Device State Dependent User Interface Management" filed Sep. 17, 2013 which is entirely incorporated herein by reference.

Implementation of Sensor Device, Secondary Device and Other Considerations

FIG. 10 shows an example of a portable biometric monitoring device having a user interface including a button and a display. Biometric tracking device 1002 includes a display 1020 and a button 1022. Biometric tracking device 1002 may collect one or more types of physiological and/or environmental data from embedded sensors and/or external devices and communicate or relay such information to other devices. The user of the biometric tracking device 1002 may utilize the button 1022 to interface with the device. The display 1020 may be a pixelated display such as an LED display. The display 1020 may display information including physiological information of the user, environmental data, the global position of the biometric tracking device 1002, battery life remaining of the biometric tracking device 1002, and other types of data.

Figure 11:
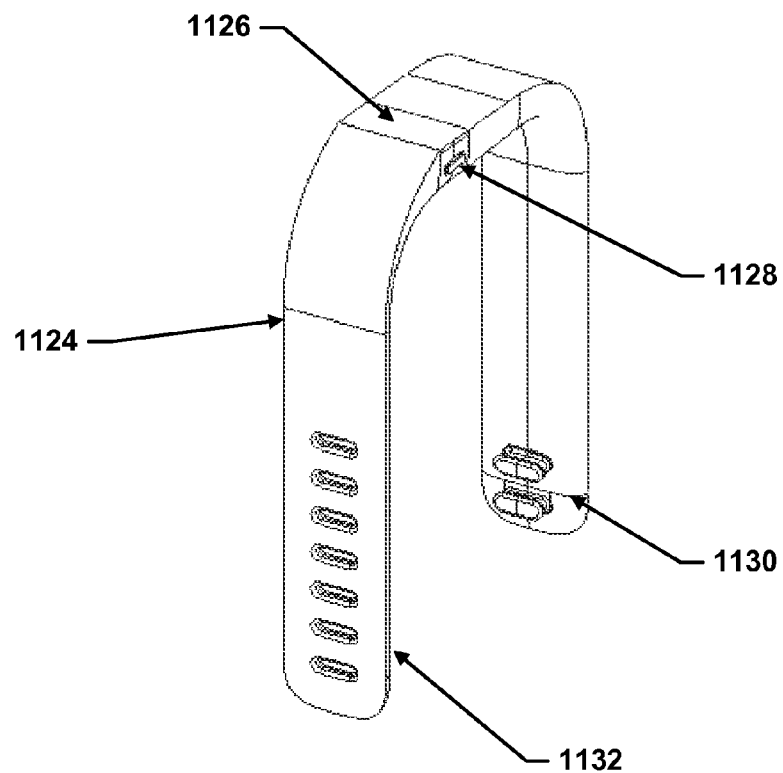
FIG. 11 shows a wrist mounted portable biometric monitoring device having a button, a display, and a band to secure the portable biometric monitoring device to the wrist.

FIG. 11 shows a wrist mounted portable biometric monitoring device having a button, a display, and a band to secure the portable biometric monitoring device to the wrist. The wrist-mounted portable biometric device 1124 includes a display 1126, a button 1128, clasp protrusions 1130, and clasp receptacles 1132. The wrist-mounted portable biometric device 1124 is a biometric monitoring device designed to be worn around a user's wrist. The wrist-mounted portable biometric device 1124 may be securely worn on the user's wrist by inserting the clasp protrusions 1130 into the clasp receptacles 1132. There are more clasp receptacles than clasp protrusions, allowing a user to adjust the fit of the wrist-mounted portable biometric device 1124 by varying which the insertion position of the clasp protrusions into the clasp receptacles.

The button 1128 is an interface for the user to interact with the wrist-mounted portable biometric device 1124. The display 1126 may display information related to the capabilities of the wrist-mounted portable biometric device 1124, similar to the display in FIG. 10.

Figure 12:
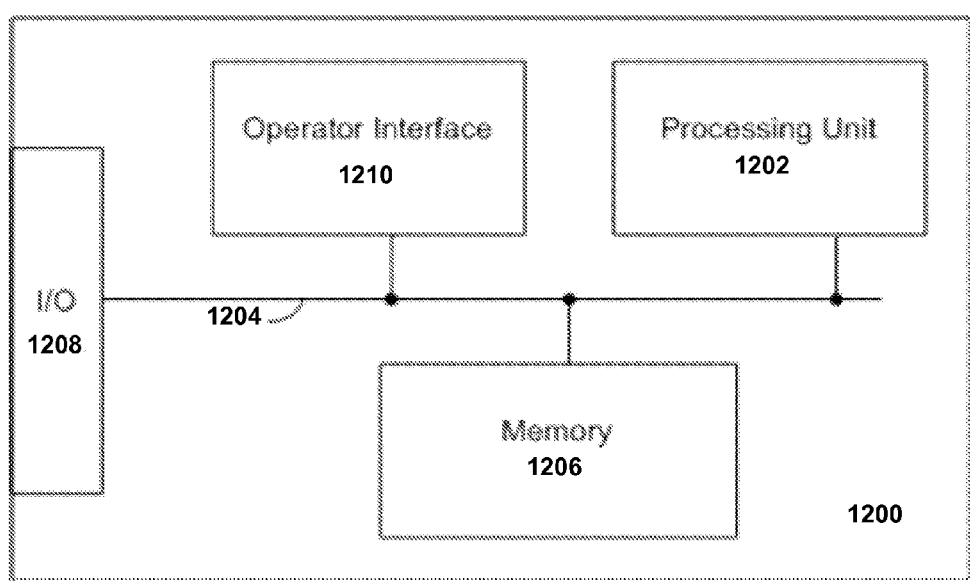
FIG. 12 shows a generalized embodiment of a computing device that may be used to implement a portable biometric monitoring device, secondary device (e.g. smartphone) and/or server or other device in which the various operations described herein may be executed.

FIG. 12 illustrates a generalized embodiment of a computing device 1200 that may be used to implement a sensor device, secondary device, and/or server or other device in which the various operations described above may be executed (e.g., in a distributed manner between the sensor device and communication device). As shown, computing device 1200 includes a processing unit 1202, memory 1206 for storing program code executed by the processing unit to effect the various methods and techniques of the above-described embodiments, and also to configuration data or other information for effecting various programmed or configuration settings in accordance with the embodiments described above. Note that the processing unit itself may be implemented by a general or special purpose processor (or set of processing cores) and thus may execute sequences of programmed instructions to effectuate the various operations associated with sensor device syncing, as well as interaction with a user, system operator or other system components.

Still referring to FIG. 12, computing device 1200 further includes one or more input and/or output (I/O) ports 1208 for receiving and outputting data (e.g., various wireless communications interfaces in accordance with communications standards described above), and a operator interface 1210 to present (display) and receive information to a human or artificial operator and thus enable an operator to control server-side and/or client-side inputs in connection with the above-described syncing operations. Though not shown, numerous other functional blocks may be provided within computing device 1200 according to other functions it may be required to perform (e.g., one or more biometric sensors, environmental sensors, etc., within a sensor device, as well as one or more wireless telephony operations in a smartphone, and wireless network access in a mobile computing device, including a smartphone, tablet computer, laptop computer, etc.) and the computing device itself may be a component in a larger device, server or network of devices and/or servers. Further, the functional blocks within computing device JJ00 are depicted as being coupled by a communication path 1204 which may include any number of shared or dedicated buses or signaling links. More generally, the functional blocks shown may be interconnected in a variety of different architectures and individually implemented by a variety of different underlying technologies and architectures. With regard to the memory architecture, for example, multiple different classes of storage may be provided within memory 1206 to store different classes of data. For example, memory 1206 may include non-volatile storage media such as fixed or removable magnetic, optical, or semiconductor-based recording media to store executable code and related data, volatile storage media such as static or dynamic RAM to store more transient information and other variable data.

Figure 13:
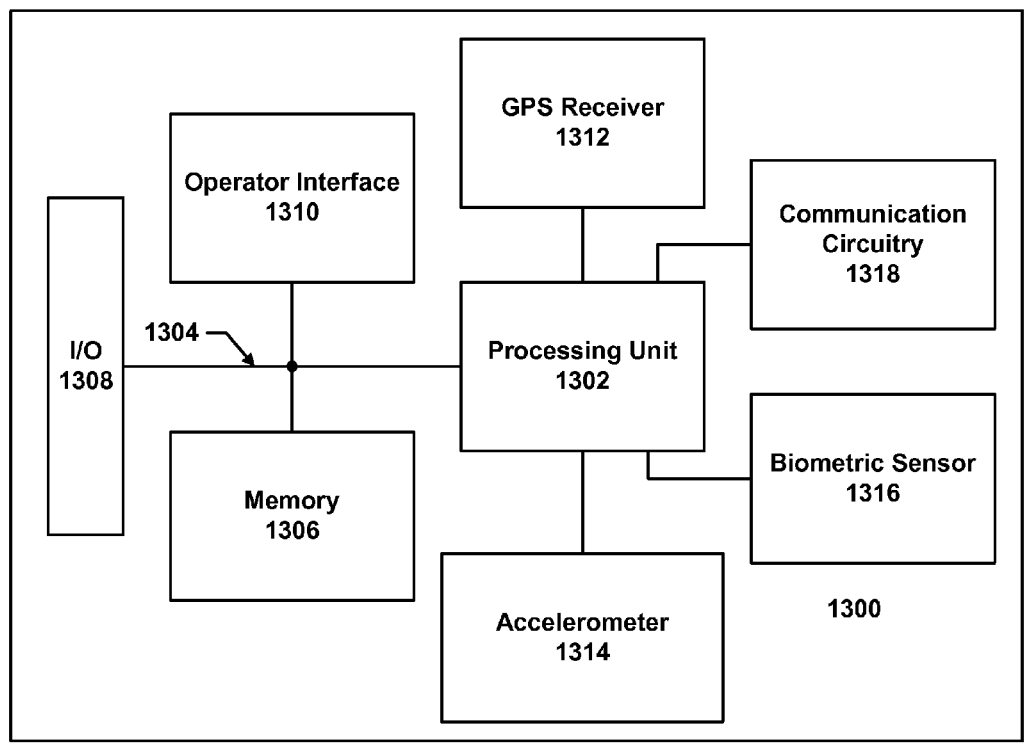
FIG. 13 shows a further generalized embodiment of a computing device that may be used to implement a portable biometric monitoring device in which the various operations described herein may be executed.

FIG. 13 shows a further generalized embodiment of a computing device that may be used to implement a portable biometric monitoring device in which the various operations described herein may be executed. The computing device 1300 includes a processing unit 1302, communication path 1304, a memory 1306, an I/O 1308, an operator interface 1310, a GPS receiver 1312, an accelerometer 1314, and a biometric sensor 1316, and communication circuitry 1318. The computing device 1300 may be similar in configuration to the computing device 1200 in FIG. 12. The computing device 1300 has the GPS receiver 1312, the accelerometer 1314, the biometric sensor 1316, and the communication circuitry 1318 coupled to the processing unit 1302. In other embodiments, one or more of the GPS receiver 1312, the accelerometer 1314, the biometric sensor 1316, and the communication circuitry 1318 may be coupled to the communication path 1304 or to other blocks in computing device 1300.

Referring again to the embodiment shown in FIG. 13, the memory 1306 may contain code or other logic for the processing unit 1302 to control the GPS receiver 1312, the accelerometer 1314, and the biometric sensor 1316. Functions that may be controlled by the logic include tracking of physiological data by the biometric sensor 1316, the communication of ephemeris data through the communication circuitry 1318, the communication of position fixing data by the GPS receiver 1312 and/or the communication circuitry 1318, and the tracking of acceleration of the portable biometric monitoring device by the accelerometer 1314.

The various methods and techniques disclosed herein may be implemented through execution of one or more a sequences of instructions (i.e., software program(s)) within processing unit 1202, or by a custom-built hardware ASIC (application-specific integrated circuit), or programmed on a programmable hardware device such as an FPGA (field-programmable gate array), or any combination thereof within or external to processing unit 1202.

Any of the various methodologies disclosed herein and/or user interfaces for configuring and managing same may be implemented by machine execution of one or more sequences instructions (including related data necessary for proper instruction execution). Such instructions may be recorded on one or more computer-readable media for later retrieval and execution within one or more processors of a special purpose or general purpose computer system or consumer electronic device or appliance, such as the system, device or appliance described in reference to Figure JJ. Computer-readable media in which such instructions and data may be embodied include, but are not limited to, non-volatile storage media in various forms (e.g., optical, magnetic or semiconductor storage media) and carrier waves that may be used to transfer such instructions and data through wireless, optical, or wired signaling media or any combination thereof. Examples of transfers of such instructions and data by carrier waves include, but are not limited to, transfers (uploads, downloads, e-mail, etc.) over the Internet and/or other computer networks via one or more data transfer protocols (e.g., HTTP, FTP, SMTP, etc.).

What is claimed is:

1. A method of determining a global position of a worn biometric monitoring device, the method comprising:
    (a) repeatedly and automatically syncing the worn biometric monitoring device with a secondary device associated with the worn biometric monitoring device, wherein the syncing comprises providing the worn biometric monitoring device with current ephemeris data from the secondary device using a wireless short-range, low-power communication protocol and each syncing comprises:
        (i) determining an elapsed time from when the ephemeris data was last updated,
        (ii) comparing the elapsed time with a sync time threshold,
        (iii) determining that the elapsed time exceeds the sync time threshold, and
        (iv) obtaining updated ephemeris data from the secondary device.

2. The method of claim 1, further comprising:
    (b) determining that a global position of the worn biometric monitoring device should be calculated; and
    (c) calculating the global position of the worn biometric monitoring device using the ephemeris data obtained in (a), wherein at least some of the syncing is conducted when the worn biometric monitoring device is not determining the global position of the worn biometric monitoring device.

3. The method of claim 1, wherein the sync time threshold is between about every 5 minutes to about every 6 hours.

4. The method of claim 1, wherein the worn biometric monitoring device is regularly synced with the secondary device according to a schedule.

5. The method of claim 4, wherein the schedule is a time schedule according to a time of day.

6. The method of claim 4, further comprising determining the schedule by monitoring a pattern of interaction of a user with the biometric monitoring device.

7. The method of claim 1, the method further comprising:
    (d) determining, before (a), that the worn biometric monitoring device is associated with the secondary device.

8. A wearable biometric monitoring device, the wearable biometric monitoring device comprising:
    communication circuitry, the communication circuitry configured to receive ephemeris data from a secondary device associated with the wearable biometric monitoring device via a wireless short-range, low-power communication protocol and output the ephemeris data to a controller; and the controller comprising one or more processors and a memory, wherein the one or more processors, the memory, and the communication circuitry, are communicatively connected and the memory is configured to store ephemeris data and program instructions for controlling the one or more processors to:
(a) repeatedly and automatically sync the wearable biometric monitoring device with the secondary device, wherein the sync comprises:
   (i) determining an elapsed time from when the ephemeris data was last updated;
   (ii) comparing the elapsed time with a sync time threshold;
   (iii) determining that the elapsed time exceeds the sync time threshold; and
   (iv) obtaining updated ephemeris data from the secondary device,
(b) determine that a global position of the wearable biometric monitoring device should be calculated, and
(c) calculate the global position using the current ephemeris data obtained in (a), wherein at least some of the syncing is conducted when the wearable biometric monitoring device is not determining the global position of the wearable biometric monitoring device.

9. The wearable biometric monitoring device of claim 8, wherein the sync time threshold is between about every 5 minutes to about every 6 hours.

10. The wearable biometric monitoring device of claim 8, wherein the program instructions for (a) further comprise instructions for regularly syncing with the secondary device according to a schedule.

11. The wearable biometric monitoring device of claim 10, wherein the schedule is a time schedule according to a time of day.

12. The wearable biometric monitoring device of claim 10, further comprising program instructions for determining the schedule by monitoring a pattern of interaction of a user with the biometric monitoring device.

13. The wearable biometric monitoring device of claim 8, wherein the memory stores further program instructions for controlling the one or more processors to:
   (d) determine, before (a), that the worn biometric monitoring device is associated with the secondary device.

* * * * *